(12) United States Patent
Lingo

(10) Patent No.: US 11,484,921 B2
(45) Date of Patent: Nov. 1, 2022

(54) BIOMASS STABILIZATION ASSEMBLY FOR MANAGING SOFT CELL ORGANIC MATERIAL

(71) Applicant: Kenneth B. Lingo, Traverse City, MI (US)

(72) Inventor: Kenneth B. Lingo, Traverse City, MI (US)

(*) Notice: Subject to any disclaimer, the term of this patent is extended or adjusted under 35 U.S.C. 154(b) by 0 days.

(21) Appl. No.: 17/503,539

(22) Filed: Oct. 18, 2021

(65) Prior Publication Data

US 2022/0118490 A1    Apr. 21, 2022

Related U.S. Application Data

(60) Provisional application No. 63/094,026, filed on Oct. 20, 2020.

(51) Int. Cl.

| | | |
|---|---|---|
| *B09B 3/40* | (2022.01) | |
| *F26B 9/00* | (2006.01) | |
| *F26B 11/00* | (2006.01) | |
| *F26B 23/10* | (2006.01) | |
| *F26B 25/16* | (2006.01) | |
| *A61L 2/04* | (2006.01) | |
| *C10B 1/02* | (2006.01) | |

(52) U.S. Cl.
CPC ............... *B09B 3/40* (2022.01); *F26B 9/003* (2013.01); *F26B 11/00* (2013.01); *F26B 23/10* (2013.01); *F26B 25/16* (2013.01); *A61L 2/04* (2013.01); *C10B 1/02* (2013.01)

(58) Field of Classification Search
CPC .... F26B 9/003; F26B 9/00; F26B 9/08; F26B 9/082; F26B 11/00; F26B 23/10; F26B 25/04; F26B 25/16; B09B 3/40; C10B 1/02; A61L 2/04
See application file for complete search history.

(56) References Cited

U.S. PATENT DOCUMENTS

| | | | | |
|---|---|---|---|---|
| 2,391,441 | A | * | 12/1945 | Baer ....................... F26B 23/10 34/411 |
| 5,143,626 | A | * | 9/1992 | Nugent ................... F26B 17/20 432/24 |
| 5,335,425 | A | * | 8/1994 | Tomizawa ............ F26B 25/006 34/265 |
| 5,974,957 | A | * | 11/1999 | Ysen ...................... F26B 9/003 99/476 |
| 7,685,737 | B2 | | 3/2010 | Gorbell et al. |
| 8,246,788 | B2 | | 8/2012 | Teal et al. |
| 8,252,966 | B2 | | 8/2012 | Teal et al. |
| 8,808,508 | B2 | | 8/2014 | Rodriguez Hernandez et al. |

(Continued)

*Primary Examiner* — Jessica Yuen
(74) *Attorney, Agent, or Firm* — Dinsmore & Shohl LLP

(57) ABSTRACT

A biomass stabilization assembly for managing soft cell organic waste ingredients. Prescribed ingredients are introduced into an inner chamber of a housing, such as through a top hatch, with subsequent unloading of a completed and chemically inert product occurring through a concealed chute and a rear port exhausting H2O gas vapor. The invention includes associated control and processor based components and operates outdoors or indoors of individual facilities and may further incorporate software protocols and algorithms which permit any status monitoring or modification of operational parameters as determined by sensor inputs.

18 Claims, 24 Drawing Sheets

(56) References Cited

U.S. PATENT DOCUMENTS

| | | |
|---|---|---|
| 9,359,556 B2 | 6/2016 | Teal et al. |
| 10,017,730 B2 | 7/2018 | Uesugi et al. |
| 10,036,592 B2 | 7/2018 | Chen et al. |
| 10,553,460 B2 | 2/2020 | Zuo et al. |
| 10,596,577 B2 | 3/2020 | Mardikian |
| 10,611,977 B2 | 4/2020 | Mennell et al. |
| 10,745,647 B2 | 8/2020 | Verdugo |
| 2010/0092652 A1* | 4/2010 | Ogura ............... C10B 51/00 71/14 |
| 2010/0192786 A1 | 8/2010 | O'Brien |
| 2013/0074357 A1* | 3/2013 | Wagner, Jr. ........... F26B 25/06 34/201 |
| 2013/0326935 A1 | 12/2013 | Kimball |

* cited by examiner

BIOMASS STABILIZATION ASSEMBLY FOR MANAGING SOFT CELL ORGANIC MATERIAL

CROSS REFERENCE TO RELATED APPLICATIONS

The present application claims the priority of U.S. Ser. No. 63/094,026 filed Oct. 20, 2020.

FIELD OF THE INVENTION

The present invention relates generally to biomass stabilization assemblies and processes for managing soft cell organic materials (typically waste ingredients). More specifically, the present invention discloses an assembly for processing soft cell organic biomass not limited to vegetable and protein food waste ingredients as well as farm animal excrement into a stabilized end product, thus preventing the waste ingredients from decomposing and becoming entombed within Municipal Solid Waste Landfill Facilities MSWLF).

BACKGROUND OF THE INVENTION

The potential for adverse health hazards is known related to traditional practices of managing and entombing decomposing soft cell organic waste ingredients within existing Municipal Solid Waste Landfill Facilities (MSWLF) that has been the focus of alarm by concerned experts for decades.

By definition, decomposition is the process by which dead organic substances are broken down into simpler organic or inorganic matter such as carbon dioxide, water, simple sugars and mineral salts. The process is a part of the nutrient cycle and is essential for recycling the finite matter that occupies physical space in the biosphere.

The alarming concern of the experts is based on the fact that decomposing soft cell organic waste ingredients are not recyclable, with annual tonnage figures continually increasing at a growth rate higher than that of the human population. Additional concerns regarding conventional disposal of such organic waste include it representing a food source for vermin, bacteria and disease.

Other concerns with existing disposal methods include the continuous outgassing of carbon dioxide, methane and hydrogen sulfide by the decomposing organic waste, which also represents biologic and chemical pollutants responsible for allergens, neurological and physical diseases, including death potential for humans, wildlife and ecosystems alike. According to experts in the field, the adverse affects of decomposing soft cell organic waste ingredients do not stop once entombed within a MSWLF, but rather continue on for decades. The experts continued concern is also based on the fact that history has proven that continuously decomposing soft cell organic waste ingredients are an ever renewing food source for ever increasing populations of vermin like flea and tick infested mice and rats, the result of which translates to a health hazard with a bubonic plague (black death) potential epidemic or even a pandemic.

Traditional machines, systems and/or methods used currently to manage organic soft cell biomass waste ingredients, such as particularly but not limited to vegetable and protein food waste as well as farm animal excrement ingredients, do not have the capability to convert the organic biomass into a stabilized and chemically inert end product with an endless shelf life prospective suitable for upcycling within a relatively short span of time (such as less than twenty-four hours).

Existing methods for managing organic biomass waste ingredients include each of MSWLF (municipal solid waste landfill facility), down the drain disposal, compost machines, compost process, incineration, anaerobic digestion, aerobic digestion, and liquid compost digestion. Other past attempts for processing such biomass include attempts at freeze-drying used to transform organic biomass waste ingredients into a stabilized reduced volume and weight end product prior to it entering the state of decomposition, and prior to entering MSWLF entombment.

SUMMARY OF THE INVENTION

The present invention discloses a biomass stabilization machine and system thereof which substantively departs from conventionally traditional designs and provides a machine and system thereof primarily developed for the purpose of preventing organic biomass ingredients, particularly but not limited to vegetable and protein food waste as well as farm animal excrement ingredients, from entering the polluting stage of decomposition without additives and, as a result, converting them into a sterile dormant product with an endless shelf life prospective suitable for upcycling within hours while operating with reduced power requirements, such as without limitation under 1 kW of electrical input.

As will be described in greater detail going forward, the present invention provides a novel and non-pollutive method for stabilizing and transforming (rather than managing through progressive and long term decomposition) organic biomass waste ingredients not anticipated, suggested, implied or rendered obvious, by any of the other devices and/or processes outlined by any of the prior methods organic biomass waste management devices or processes either in part or in any combination thereof.

The present invention encompasses four electromechanical devices including each of conduction, radiant and convection heat sources, along with a forward and reversing drive mechanism and a rotisserie fitted with a duplex finger that varies the position of organic biomass waste ingredients within the inner chamber throughout the stabilization process without mastication. All devices work consecutively to stabilize the chamber's internal organic waste ingredients and are arranged to provide a singular processing device for the purpose of converting organic biomass waste ingredients into a stabilized upcycle end product with an endless shelf life prospective within a reduced processing timespan, including such as less than twenty-four hours therefore transforming the soft cell biomass from a pollutant liability to an energy, food or fertilizer asset opportunity produced at an energy consumption rate of less than 1 kW per hour.

Additional aspects of the present invention include associated control and processor based components for operating any number of individual biomass stabilization machines or systems, such as which can be placed within individual facilities (not limited to restaurants of the like). The control/processor components may further incorporate software protocols and algorithms which permit any of status monitoring or modification of operational parameters of any number of individual systems or machines, and as determined by sensor inputs. The invention can further incorporate a mobile application or other supporting platform for use on a processor driven device not limited to a smart phone or tablet.

BRIEF DESCRIPTION OF THE DRAWINGS

Reference will now be made to the attached drawings, when read in combination with the following detailed description, wherein like reference numerals refer to like parts throughout the several views, and in which.

DETAILED DESCRIPTION OF THE PREFERRED EMBODIMENTS

With reference to the attached illustrations, the present invention discloses a biomass stabilization machine and system overcoming the shortcomings associated with currently practiced traditional organic biomass waste management devises and systems for stabilizing organic food waste ingredients as well as farm animal excrement.

Another objective is to provide a machine and system thereof that can be easily tuned to accept any form of soft cell organic biomass waste or non-waste ingredients.

A further objective is to provide associated control and processor based components for operating any number of individual biomass stabilization machines or systems, such as which can be placed within individual facilities (not limited to restaurants of the like). The control/processor components may further incorporate software protocols and algorithms which permit any of status monitoring or modification of operational parameters of any number of individual systems or machines, and as determined by sensor inputs. The invention can further incorporate a mobile application or other supporting platform for use on a processor driven device not limited to a smart phone or tablet. Other objectives include providing a machine and system thereof that operates using less than 1 kw (kilowatt) and is capable of operating in either of indoor or outdoor conditions.

Figure 1:
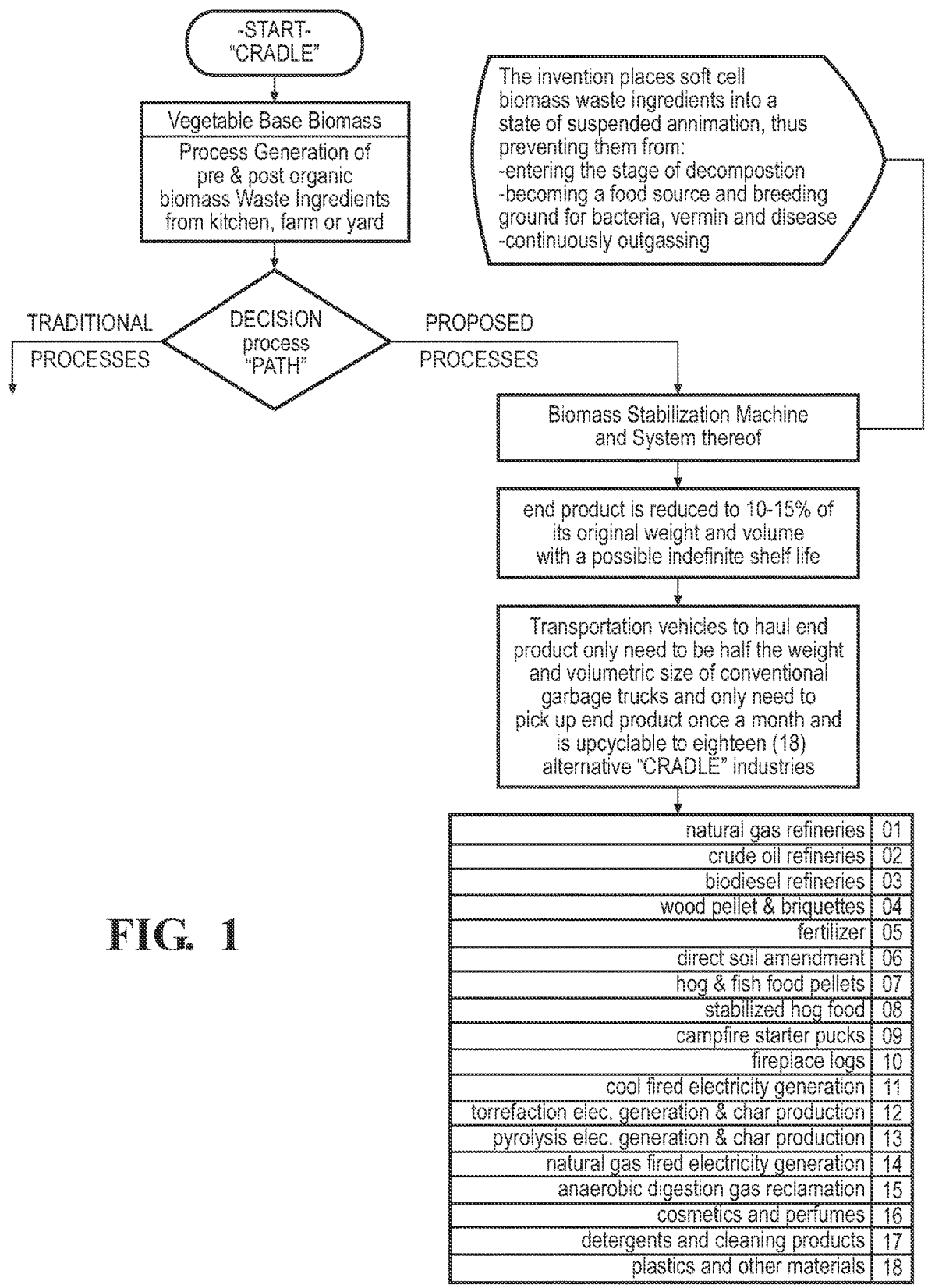
FIGS. 1, 1A and 1B provide a series of flowcharts illustrating a protocol for converting each of vegetable base organic biomass, protein based organic biomass and farm animal excrement ingredients, whereas each ingredient is prevented from entering the state of decomposition and instead converted into a stabilized upcyclable product within hours as a result of their processing by the present invention.
Figure 1A:
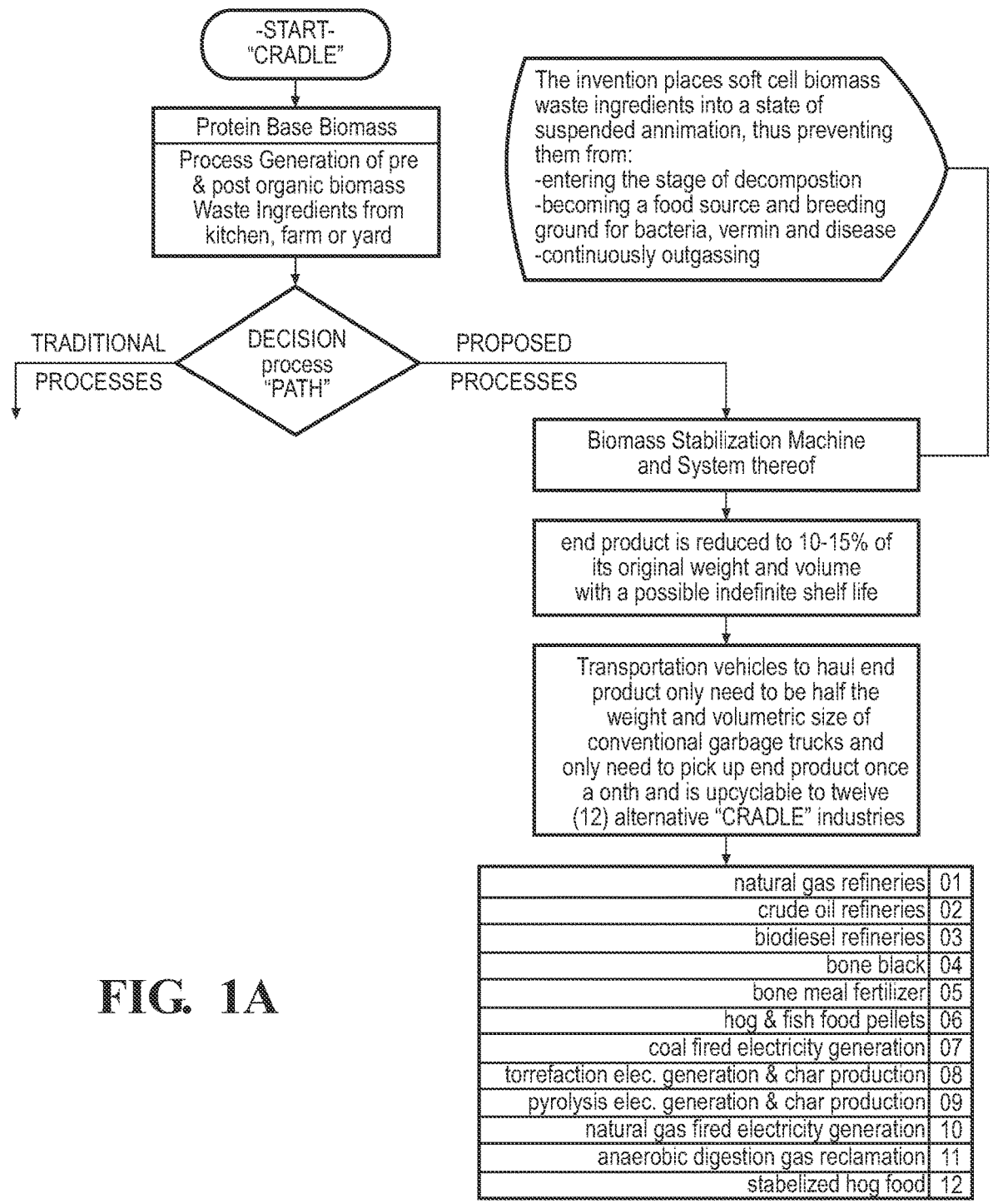
Figure 1B:
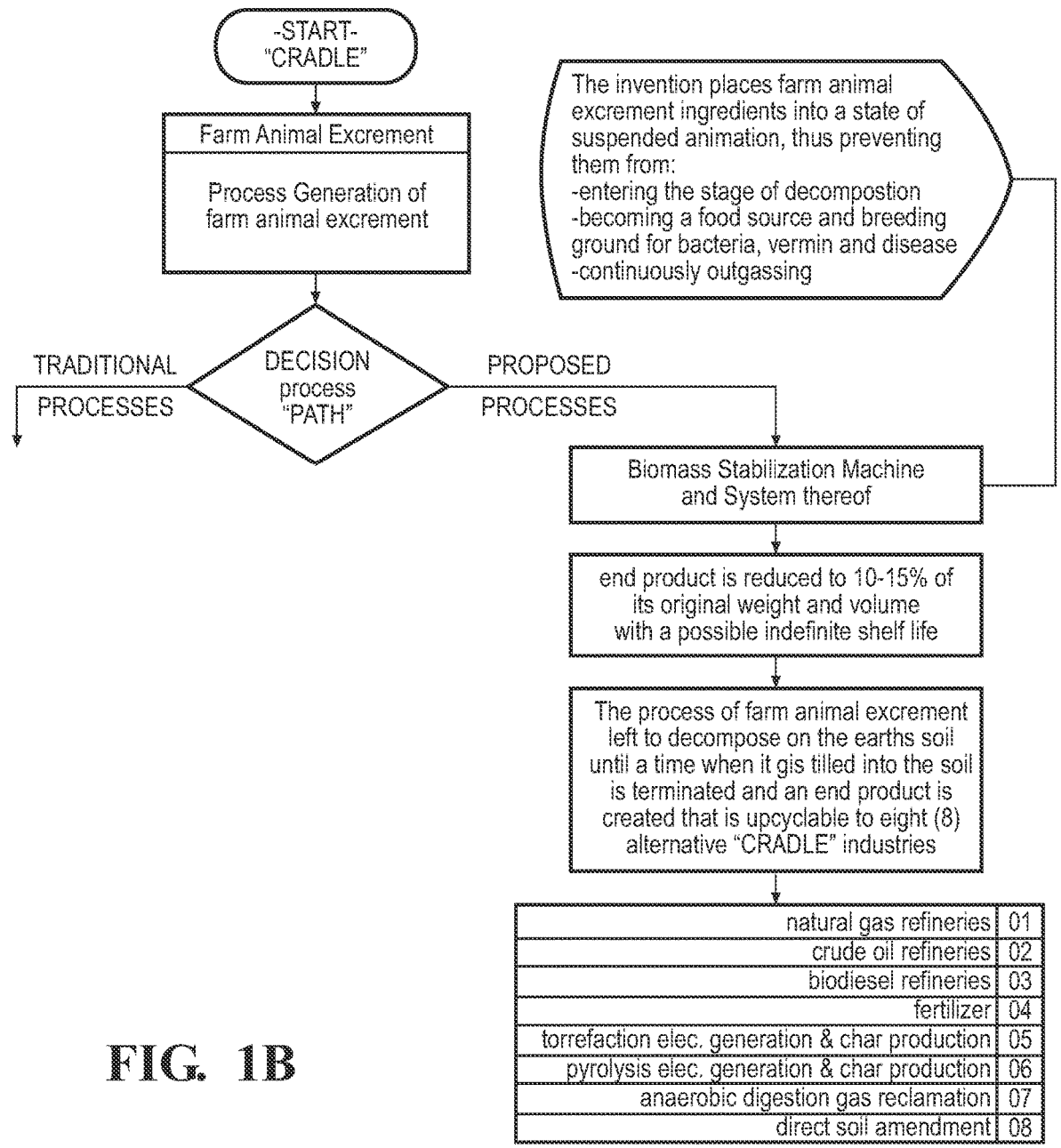

With reference initially to FIGS. 1, 1A and 1B, these collectively depict flowchart diagrams illustrating upcycle industry markets intended to supply the stabilized end product exiting the present invention. In this instance of FIG. 1, a flow process is depicted for stabilizing a vegetable base biomass, with FIG. 1A depicting a similar process for a protein based biomass and FIG. 1B for stabilizing farm animal excrement. In each of the flowcharts, the stabilization process results in a stabilized end product having a reduced weight/volume typically in a range of 10%-15% of its original weight/volume, thus enabling easy transport of the inert stabilized product for upcycled application to a number of identified potential industries.

With reference collectively to FIGS. 2-22, an additional series of drawings are provided which illustrate the biomass stabilization machine according to the present invention machine, and which includes an outer housing 100 (see FIGS. 2-9 including each of blind access cover 102, right side access cover 103, top 105, top load hatch 106, inner insulation pad 107, inner cover plate 108, key locking device 109, mounting channels 111, castor wheel frame 112, castor wheels 113, and fastener device 114). This in turn encapsulates all of the embodiment subassemblies, and again including each of the inner chamber (FIGS. 10-21 including left side panel 201, right side panel 202, center panel 203, heat compartment 204, wire way conduit crossover 205, unload hatch opening 206, unload hatch cover plate 207 and over center locking link 208).

Drive assembly (FIGS. 19-20) includes each of an electric motor 301, motor to reducer drive belt and sheaves 302, motor to reducer mounting bracket 303, speed reducer 304, speed reducer to rotisserie drive chain and sprockets 305 and drive assembly mounting bracket 306.

Rotisserie (FIGS. 10-21) includes each of rotisserie bearing 401, rotisserie shaft 402, rotisserie arm 403, and rotisserie arm duplex finger 404. Heat source (FIGS. 10-21) includes each of conduction and radiant heat source 501 (FIG. 10) and convection heat source 502 (FIGS. 15-16).

Incoming air supply (FIGS. 15-16), includes each of a manifold 601, incoming air supply piping 602, rotisserie air infusing piping 603, incoming air supply blower 604. Water gas vapor exhaust snorkel (FIGS. 17-18) includes each of H2O gas vapor exhaust snorkel piping 606, trap screen 607, and lower CFM (cubic feet per minute) fan 608.

Figure 14:
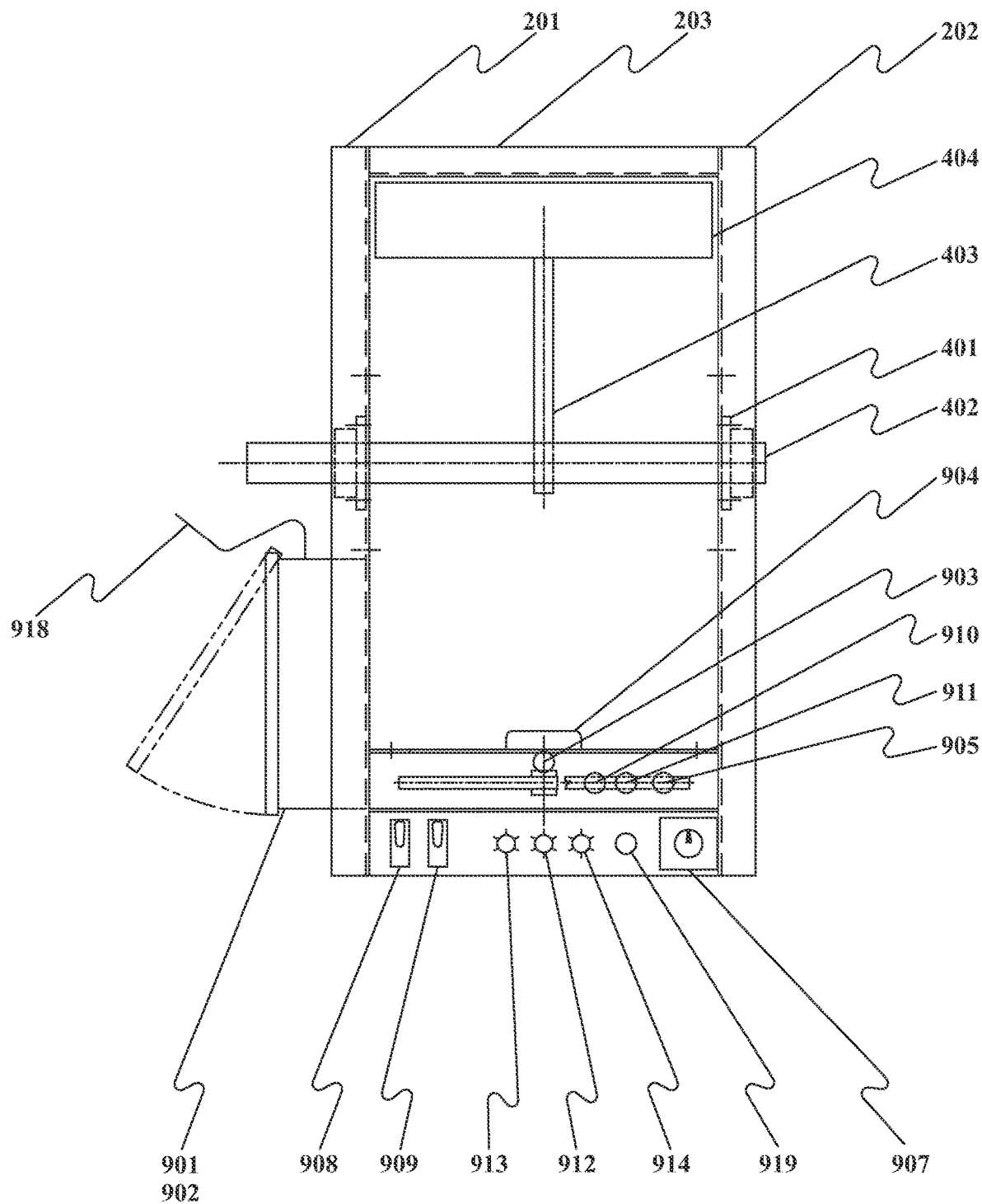
FIG. 14 is a top view of the inner chamber component of FIG. 10.
Figure 15:
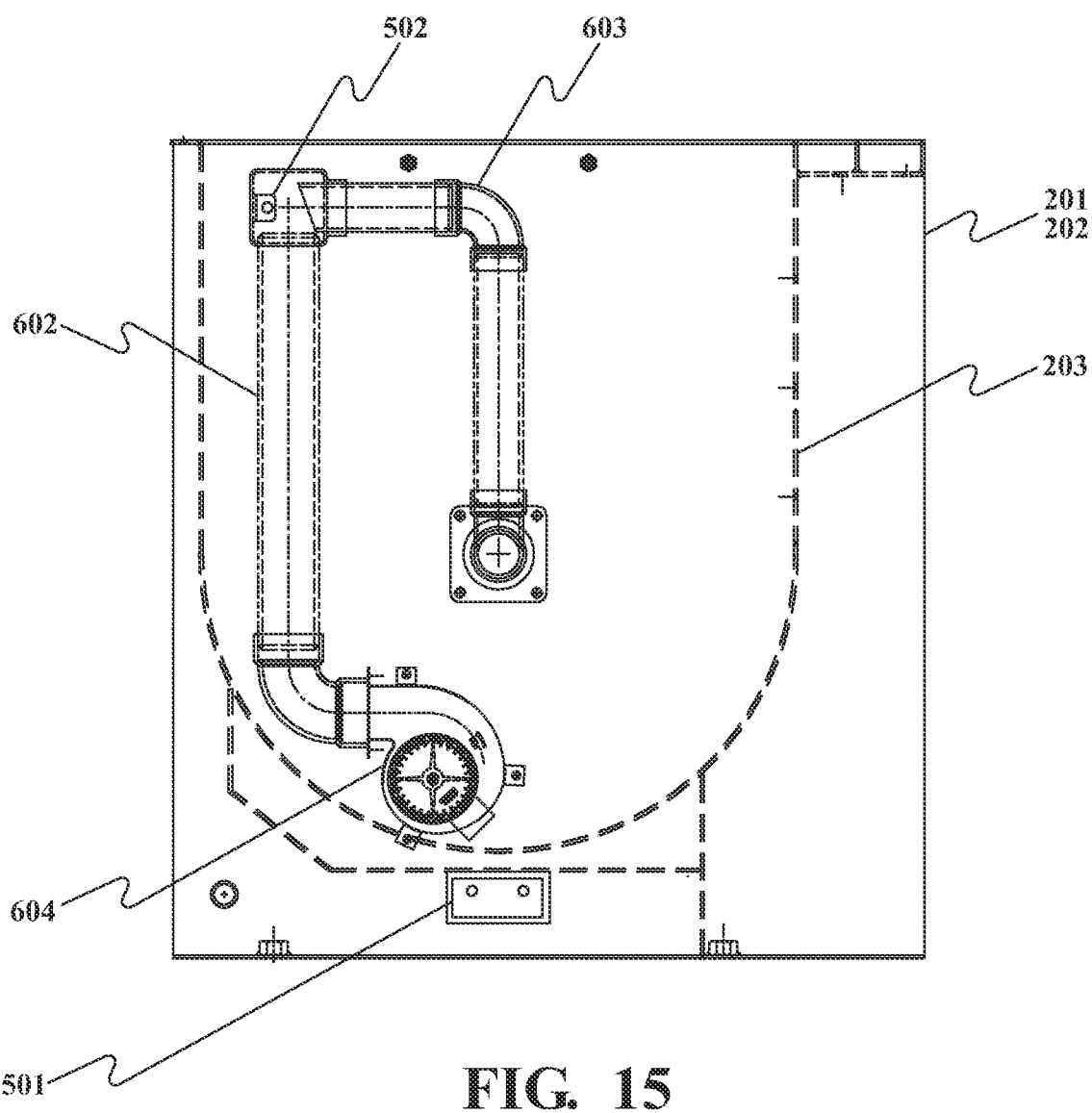
FIG. 15 is a left side view of the inner chamber component of FIG. 10 and better illustrating the features of the air entry/supply system.
Figure 16:
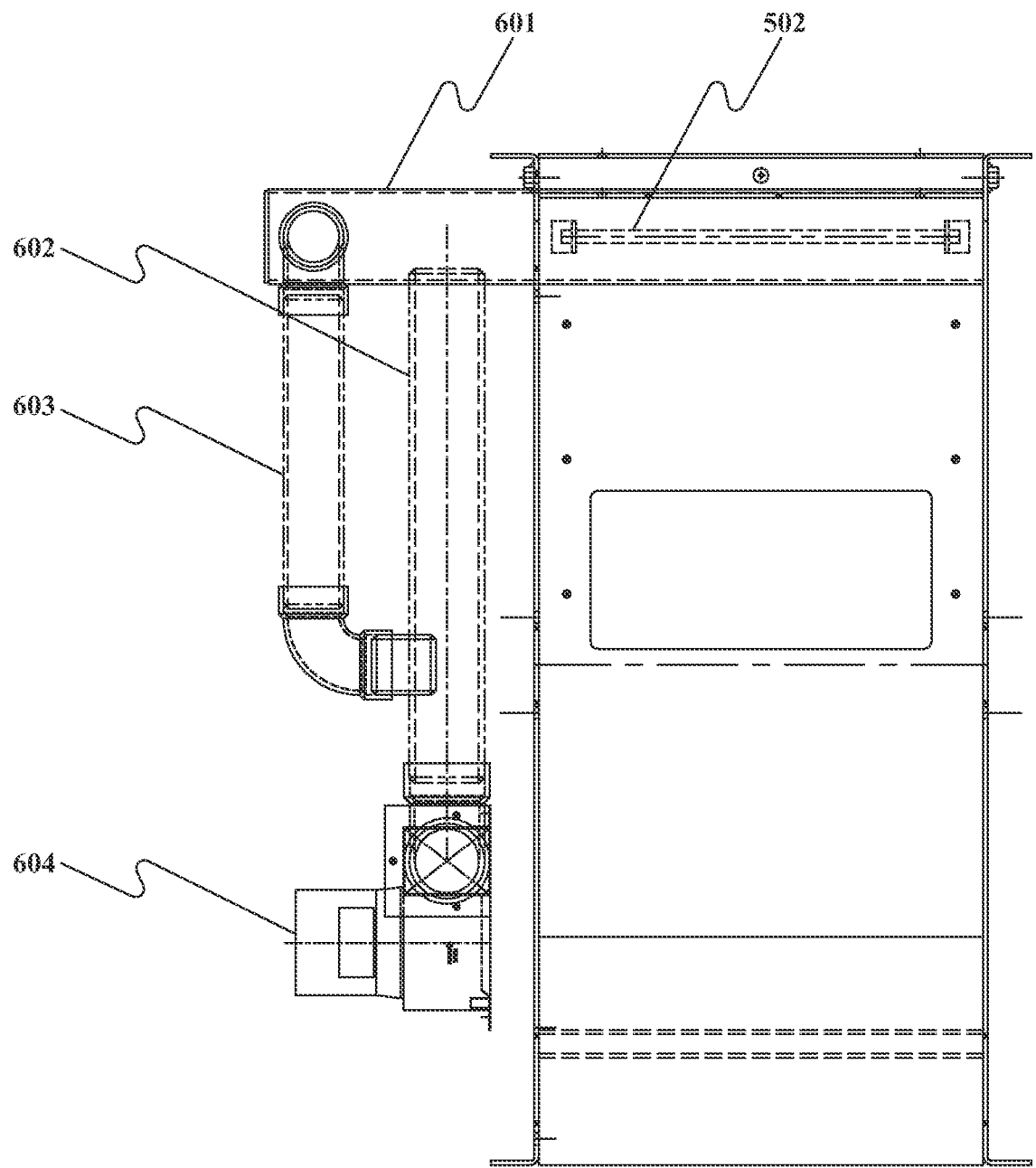
FIG. 16 is a front view of the air entry/supply of FIG. 15.
Figure 21:
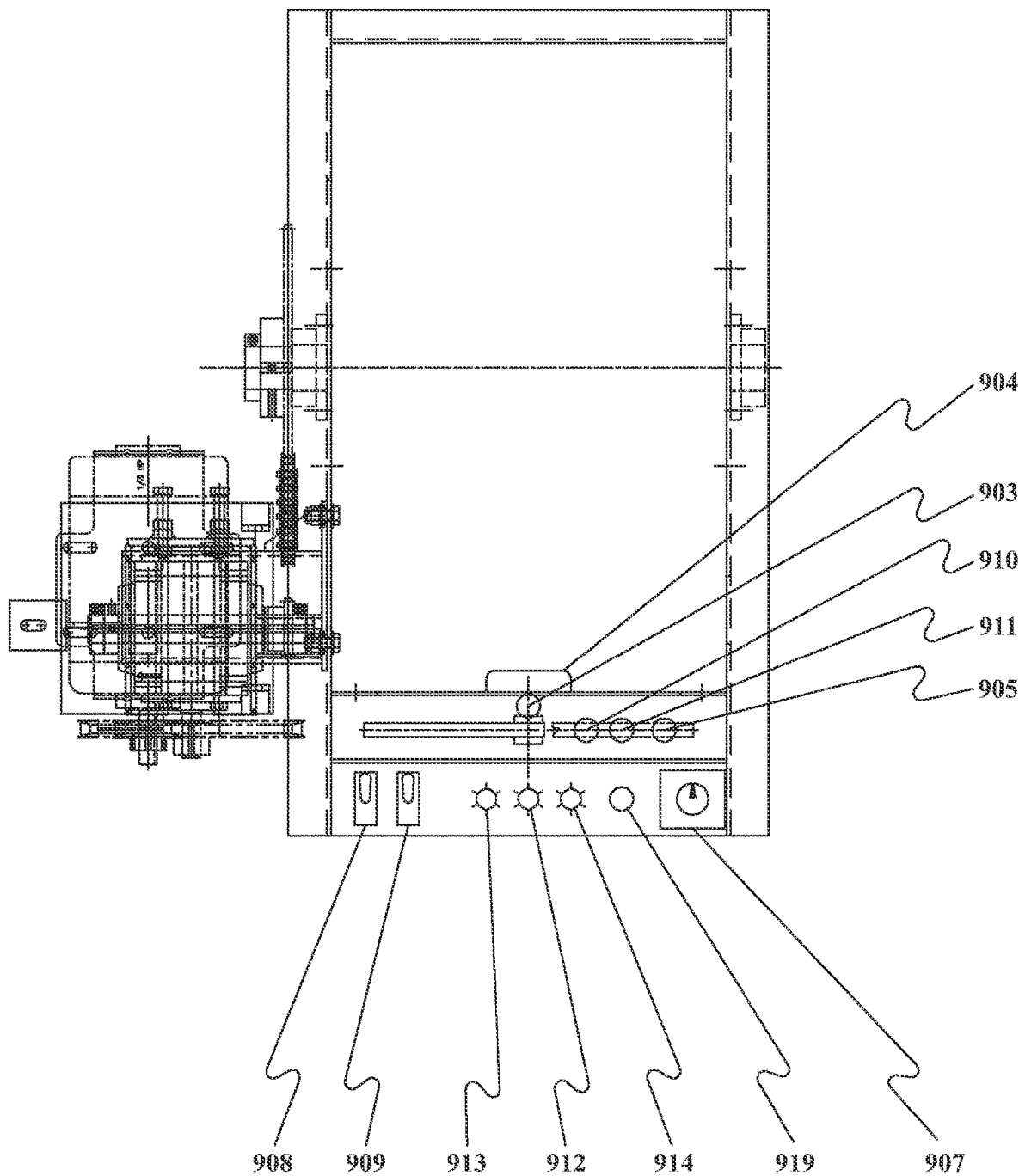
FIG. 21 is a top view of the inner chamber similar to FIG. 14 and illustrating the electrical controls systems forming a portion of the present invention.
Figure 22:
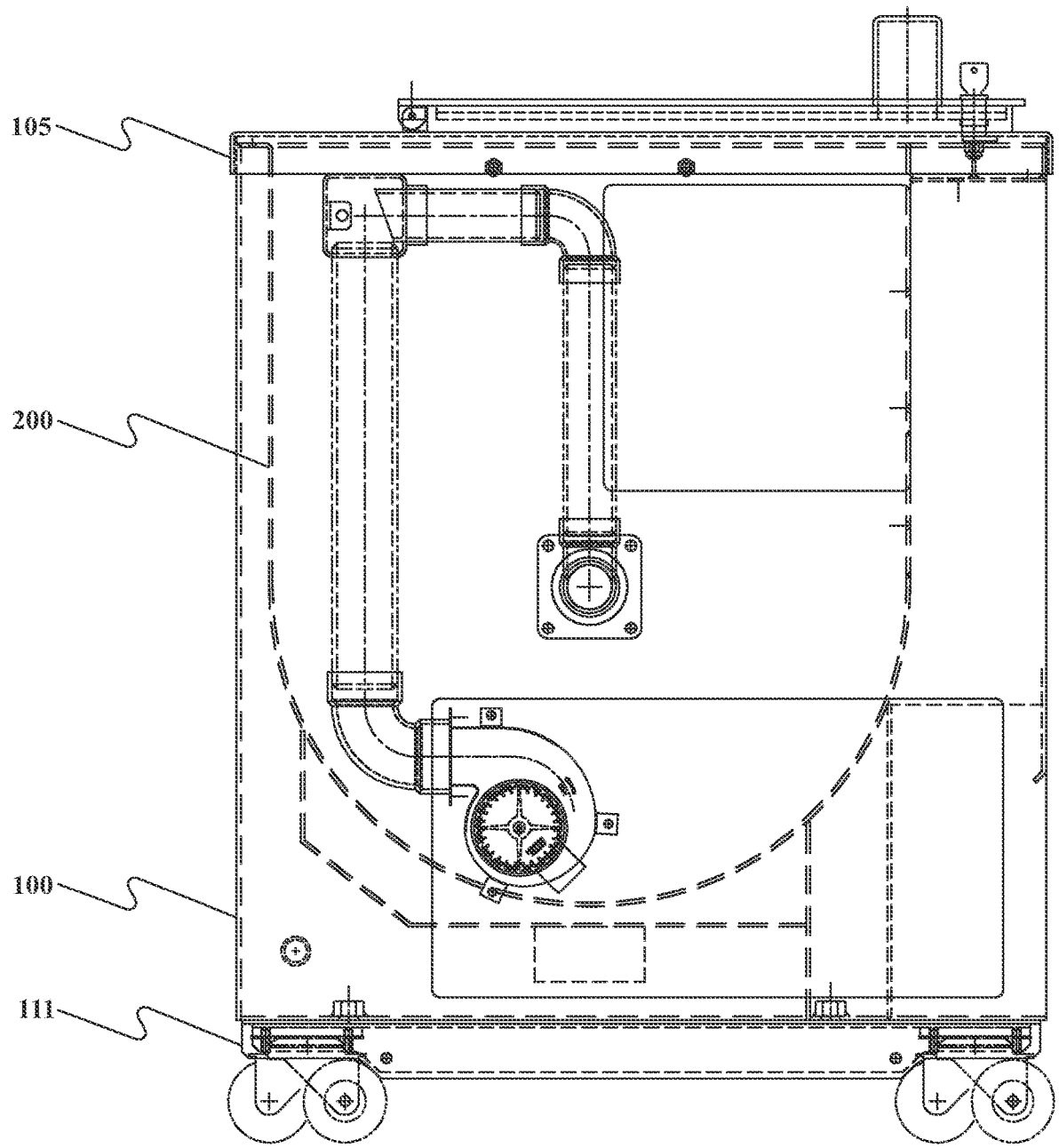
FIG. 22 is a left side view depicting both the outer housing (solid) and inner chamber (phantom) of the biomass stabilization machine.

As will also be described in reference to FIGS. 14-21, the associated controls for operating the biomass stabilization machine of the present invention include (according to one on-limiting variant) each of a Control Panel Electric Relay Control Logic 901 (FIG. 14), Control Panel Electric CNC PC Control Logic 902 (FIG. 14), Top Load Hatch Integrated Key Lock Latch and Switch 903 (FIG. 14), Top Load Hatch Integrated Inner Chamber Illuminator 904 (FIG. 21), Unload Hatch with Integrated Switch 905 (FIGS. 14 & 21), Rotisserie "HOME" Position Switch 906 (FIG. 19), Cycle Start Selector Switch 907 (FIG. 14), Selector Switch for "PROCESS" or "UNLOAD" 908 (FIG. 14), Selector Switch for "Relay Manual Electrical circuitry" or "CNC Automatic Electrical circuitry" 909 (FIG. 14), Humidity Sensor 910 (FIG. 14), Temperature Sensor 911 (FIG. 14), White "CYCLE START" illuminator 912 (FIG. 14), Red "CYCLE INTERRUPTER" Illuminator (machine jam) 913 (FIG. 14), Green "CYCLE END" Illuminator 914 (FIG. 14), Operational Drive Chain Switch 915 (FIG. 19), Operational Motor Belt Switch 916 (FIG. 20), Power Service Plug 917 (FIGS. 5 & 8), Control Panel Service Plugs and Wiring Harness 918 (FIG. 14) and Emergency Stop Button 919 (FIGS. 14 & 21).

The Outer Housing 100 is fabricated from either carbon or stainless steel and is, without limitation, cuboidal shaped by design as illustrated in FIGS. 2-9. In one non-limiting variant, the outer housing is comprised of four (4) joined sides, a joined bottom and capped with a removable overlapping top that secures to the inner chamber 200.

Figure 6:
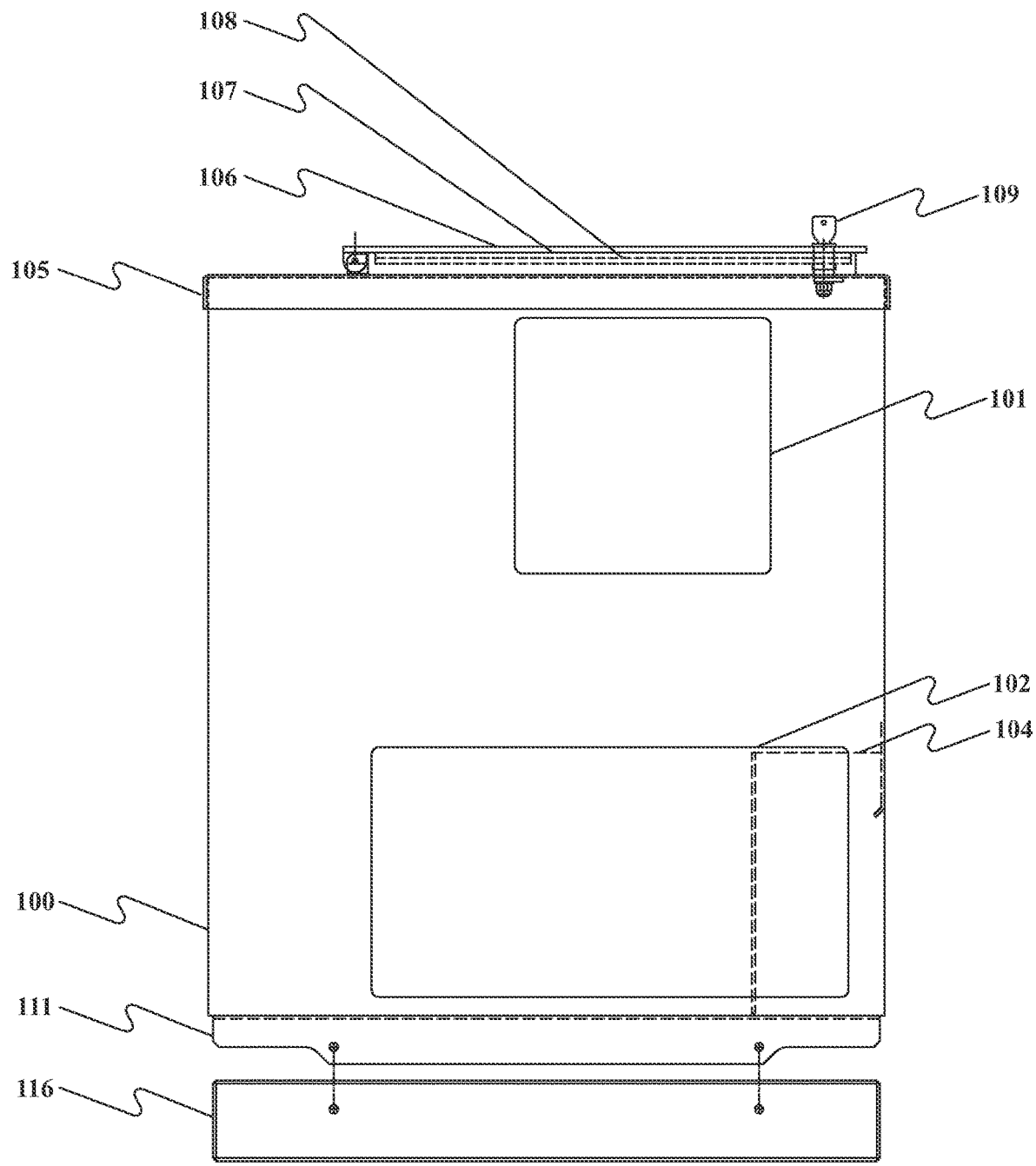
FIG. 6 is a left side view similar to FIG. 2 and depicting an alternate arrangement including non-heat conductive bunk feet intended for unit placement on soft or unstable surfaces, such as gravel and asphalt.
Figure 7:
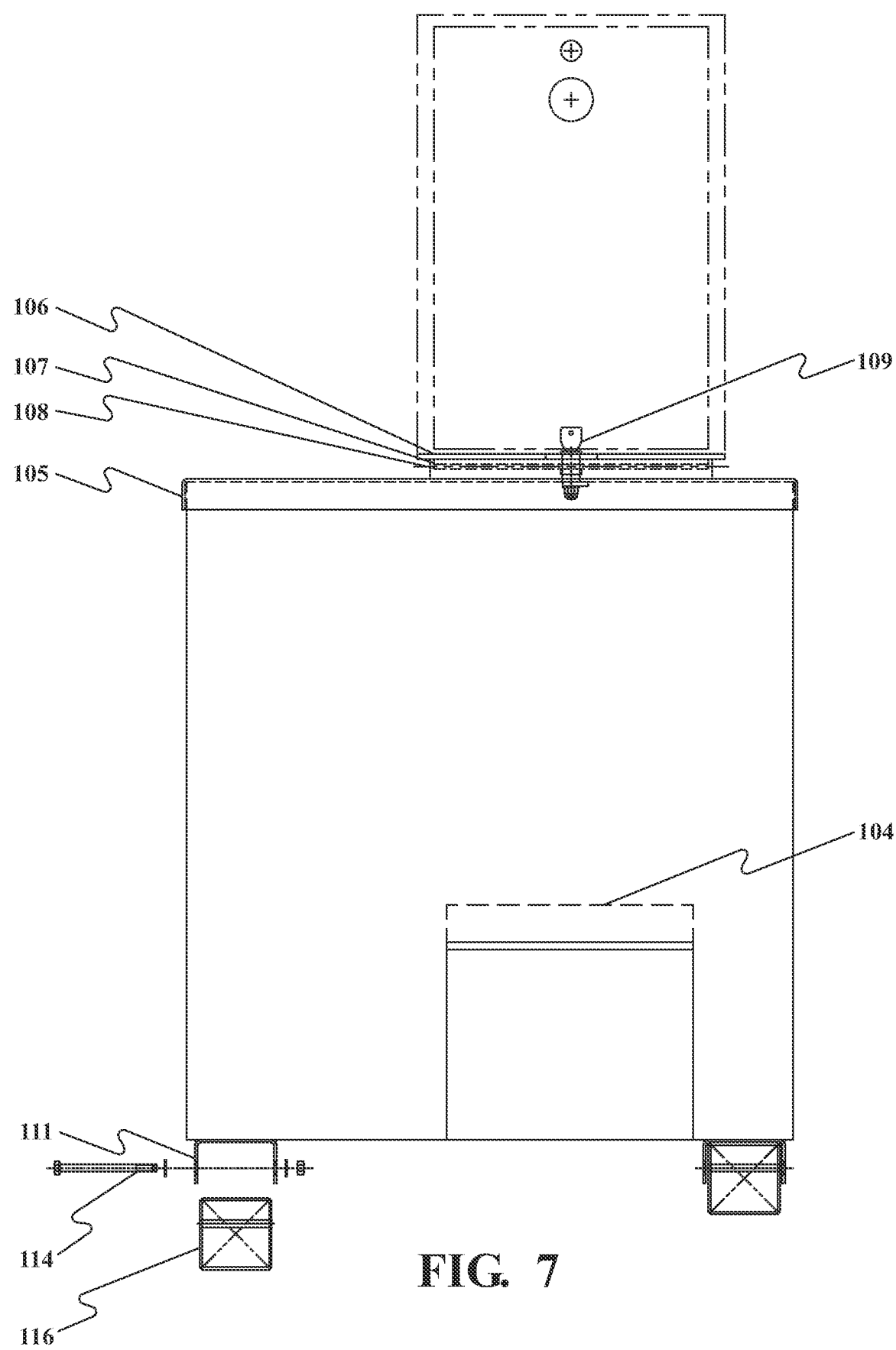
FIG. 7 is a front view of the machine in FIG. 6 with bunk feet again depicted.
Figure 8:
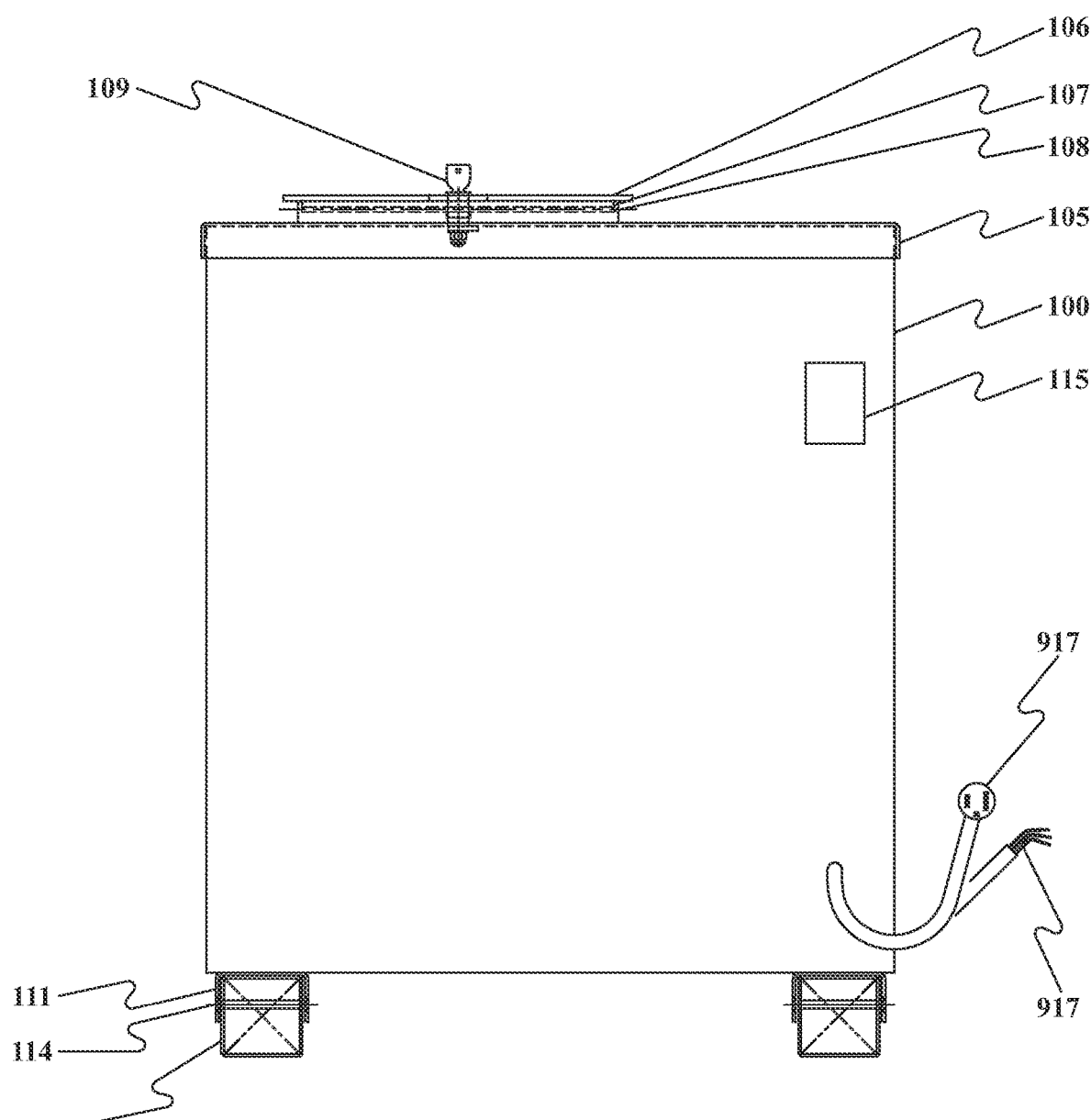
FIG. 8 is a rear view of the machine of FIGS. 6-7.
Figure 9:
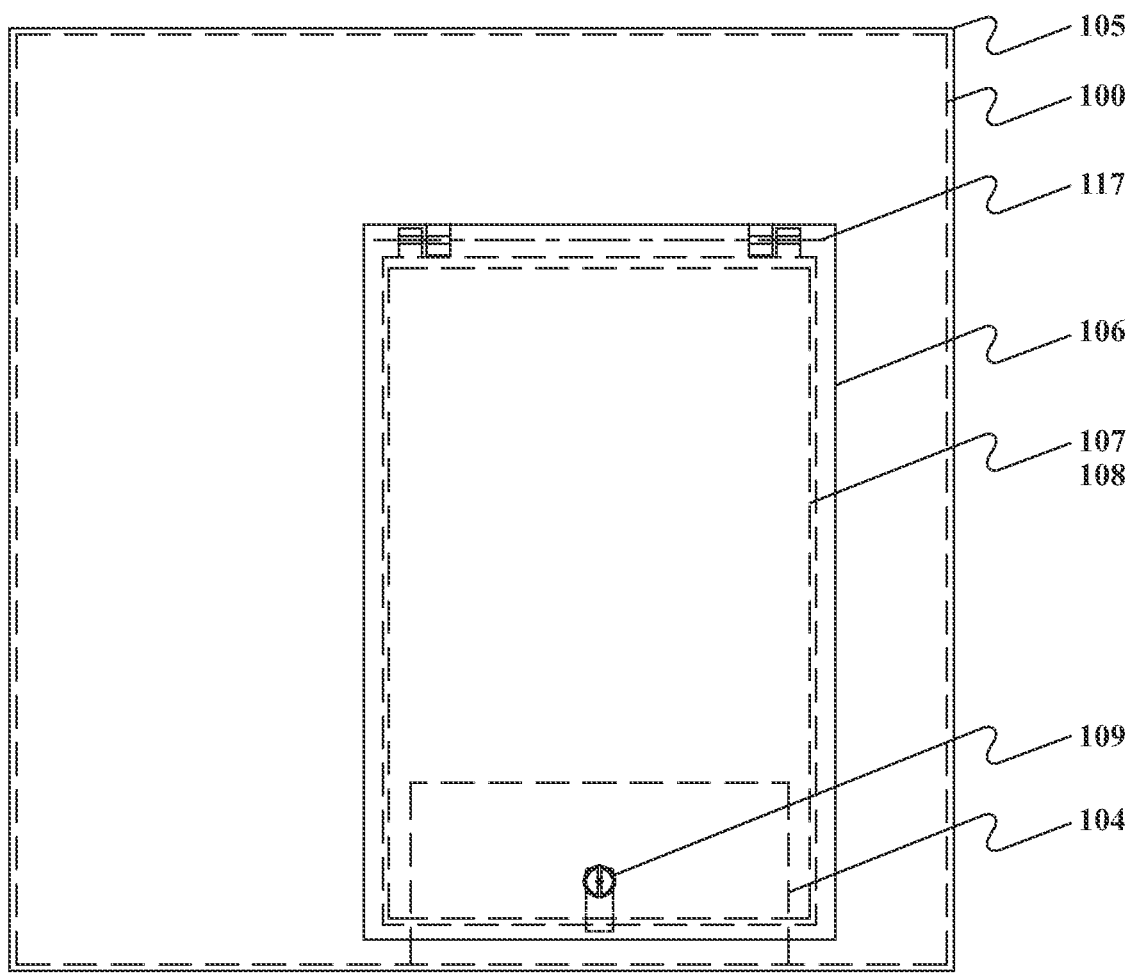
FIG. 9 is a top view of the machine of FIG. 6 and better illustrating the features of the top loading hatch.
Figure 10:
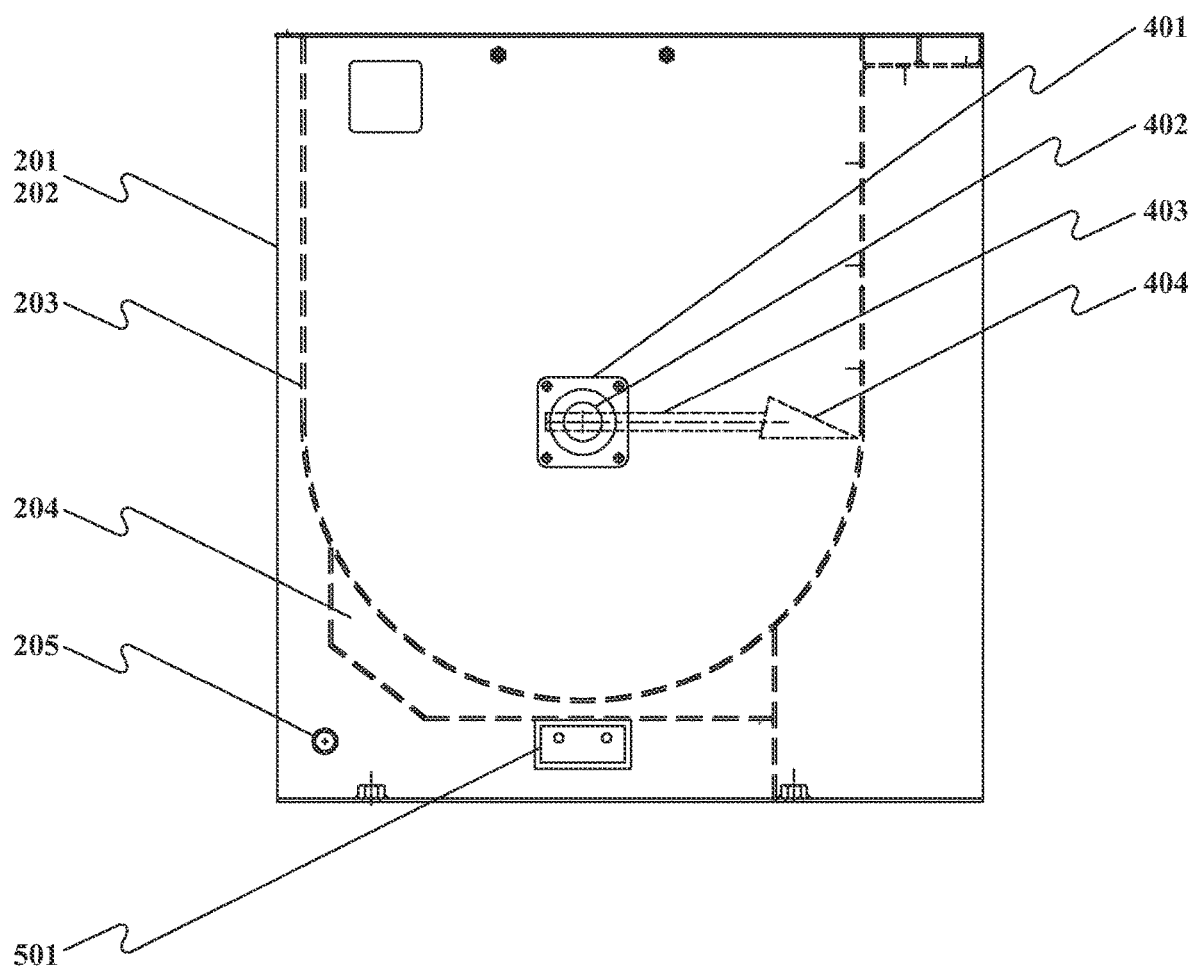
FIG. 10 is a left side view of an inner chamber component of the biomass stabilization machine and depicting the features of the inner rotisserie sub-assembly.

The outer housing 100 is fitted with either four (4) swivel caster wheels 113, two (2) frames 112 and two (2) mounting channels 111 along with mounting hardware 114 (FIGS. 2-5), an arrangement intended for unit placement on hard stable surfaces or two non-heat conductive bunks 116 intended for unit placement on soft or unstable surfaces like gravel and asphalt (FIGS. 6-8). In either case the swivel caster wheels 113 and frame 112 are interchangeable with the non-heat conductive bunks (see at 116 in FIG. 6, all mounting to the outer housing bottom brackets with two (2) of the fasteners devices 114 (FIGS. 6-8). The primary difference between the two (2) different foot configurations is that the non-heat conductive bunks 116 minimize the overall weight per U.S. square inch of the present invention.

Figure 2:
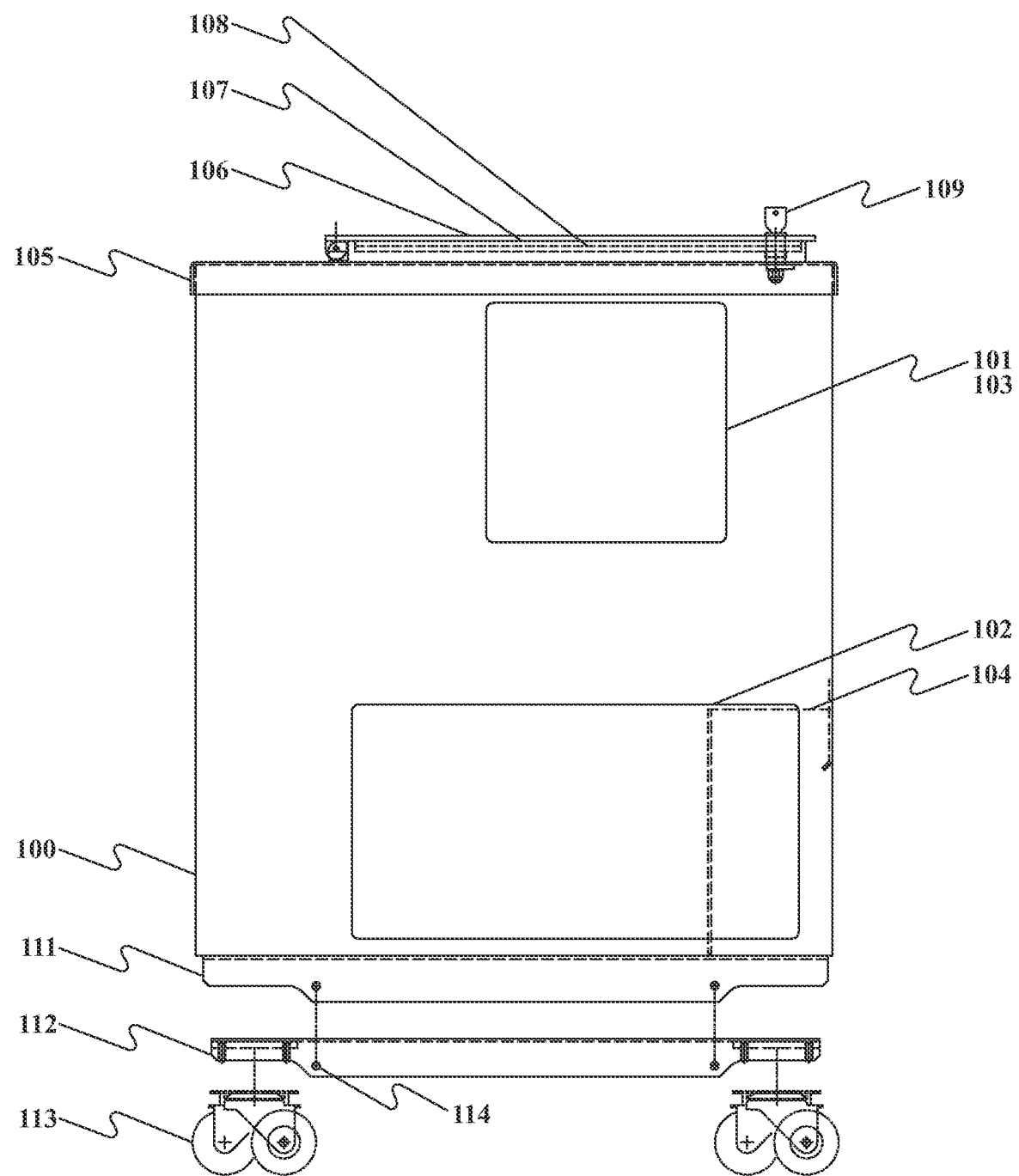
FIG. 2 is an illustration of a wheel or castor supported biomass stabilization machine outer housing according to the present invention.
Figure 3:
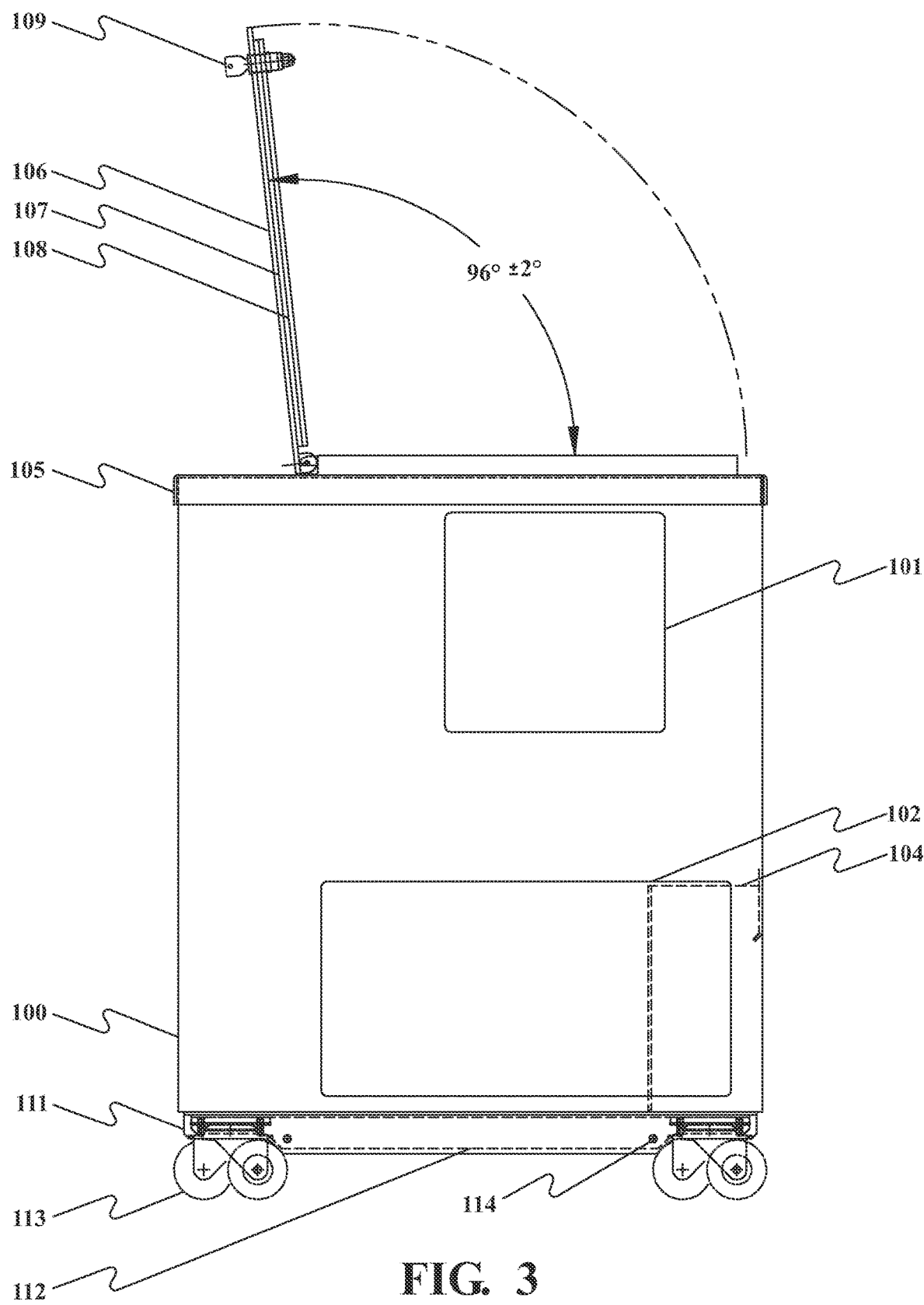
FIG. 3 is a succeeding illustration to FIG. 1 depicting the top loading hatch in an open position.
Figure 4:
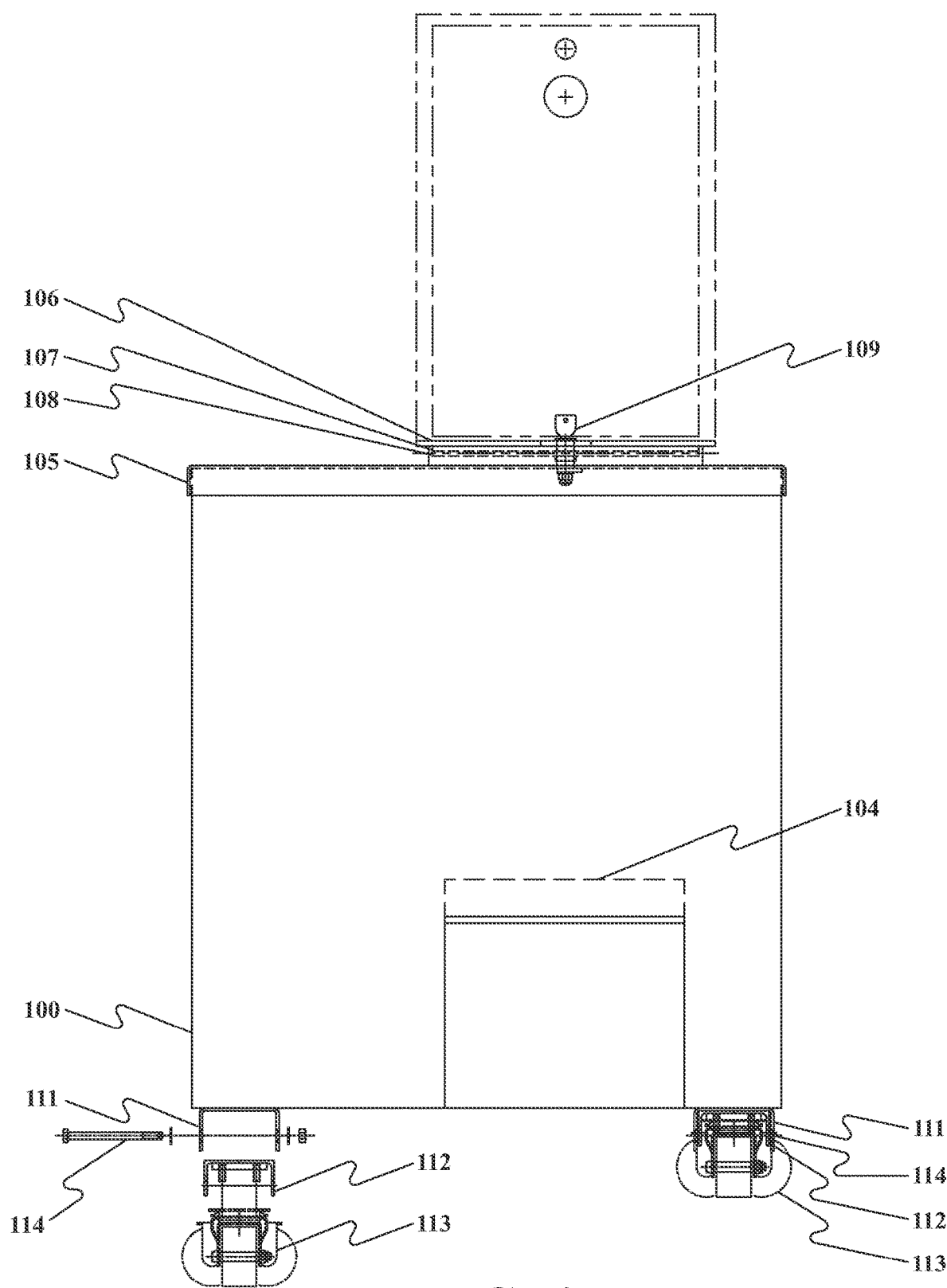
FIG. 4 is a front rotated view of FIG. 3 depicting a lower unload port for removing the inert completed product from the housing.
Figure 5:
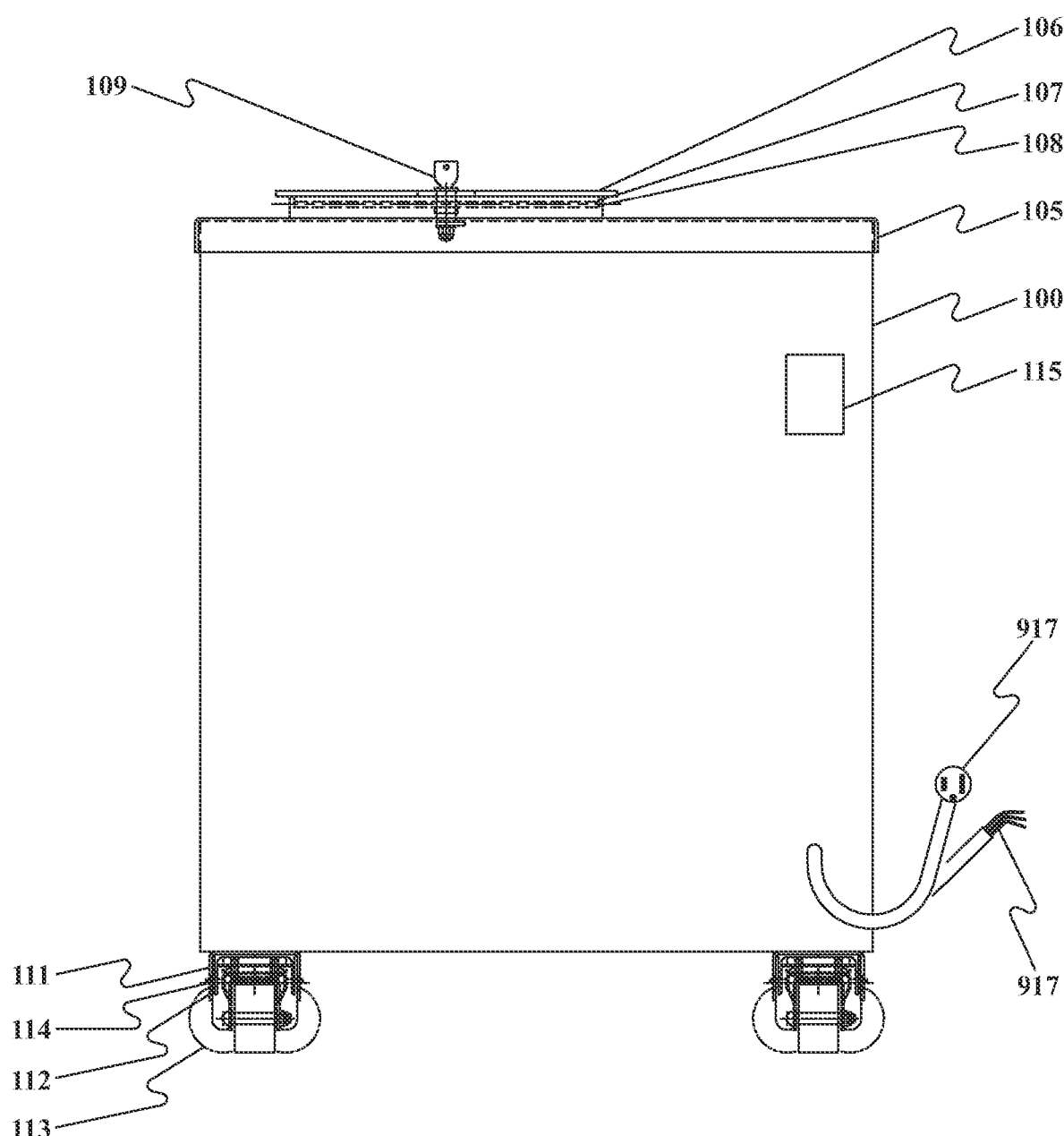
FIG. 5 is a rear view of the machine depicting the top loading hatch closed and depicting both a main power supply as well as a piggy back plug in port for coupling additional machines/units in a cooperative fashion.

The outer housing 100 has three (3) blind inner component access covers 101, 102 and 103 illustrated in (FIG. 2). Additionally, the outer housing is arranged with a concealed unload chute 104 (FIGS. 2-4, 6, 7 and 9), a removable overlapping top 105 (FIGS. 2-9) that secures to the inner chamber 200 and is arranged with a top load hatch 106 arranged with an insulation pad 107, an inner cover plate 108, a key locking device 109 (FIGS. 1-9). The rear view of FIG. 8 illustrates an electrical service plug or hardwire option 917 along with a piggyback plugin port 115 (FIGS. 5 and 8) to couple an additional duplicate unit.

Figure 11:
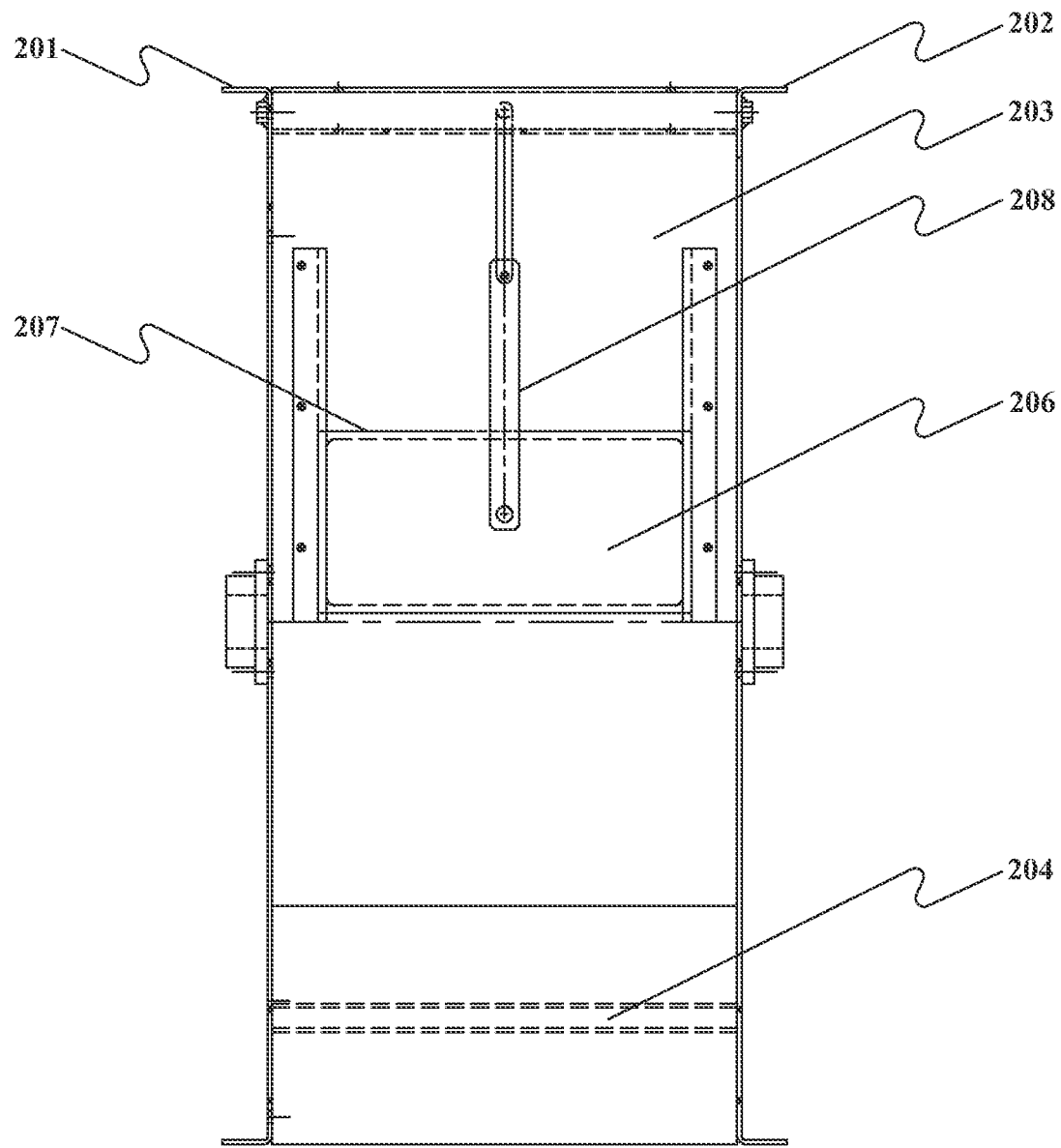
FIG. 11 is a front view of the inner chamber and depicting the unload hatch in a closed position.
Figure 12:
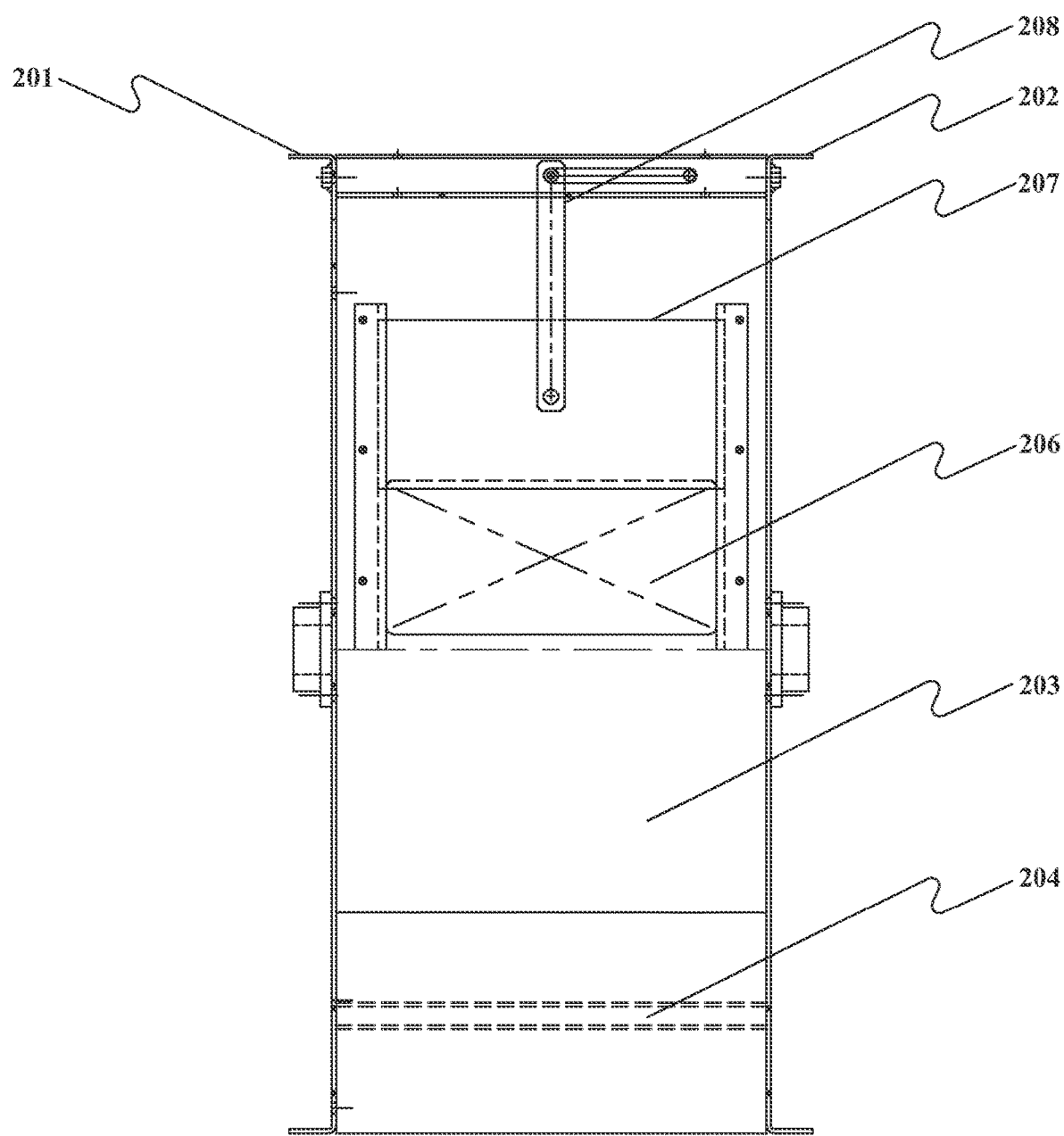
FIG. 12 is a succeeding view of FIG. 11 depicting the unload hatch in an open position.
Figure 13:
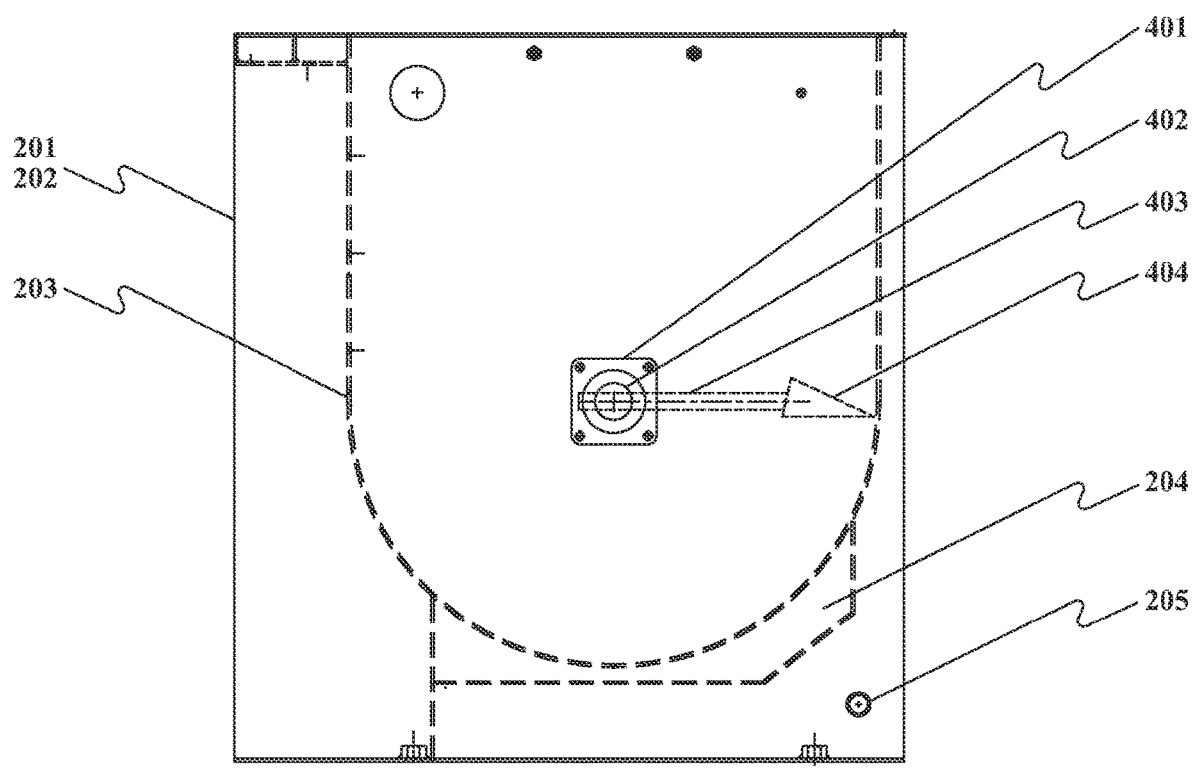
FIG. 13 is a right side view of the inner chamber of the biomass stabilization machine of FIG. 10 and depicting in phantom the rotisserie features from another direction.

The inner chamber is open on the top and becomes sealed to the outer housing 100 once the outer housing overlapping top 105 is secured in place. The inner chamber consists of four parts, two (2) side panels, one (1) each 201 left side and 202 right side, a center panel 203 with a radially formed bottom or floor which is welded water tight to the two (2) side panels thus forming a contained processing chamber, also included is heat chamber 204 (FIGS. 10-13), an insulated wire way conduit crossover 205 (FIG. 10-13), an unload hatch opening 206 (FIGS. 11 and 12), an unload hatch cover plate 207 with trap and guide rails (FIGS. 11 and 12) and an over center locking link 208 that keeps the unload hatch cover plate locked in both the opened and closed positions (FIGS. 11 and 12).

Figure 19:
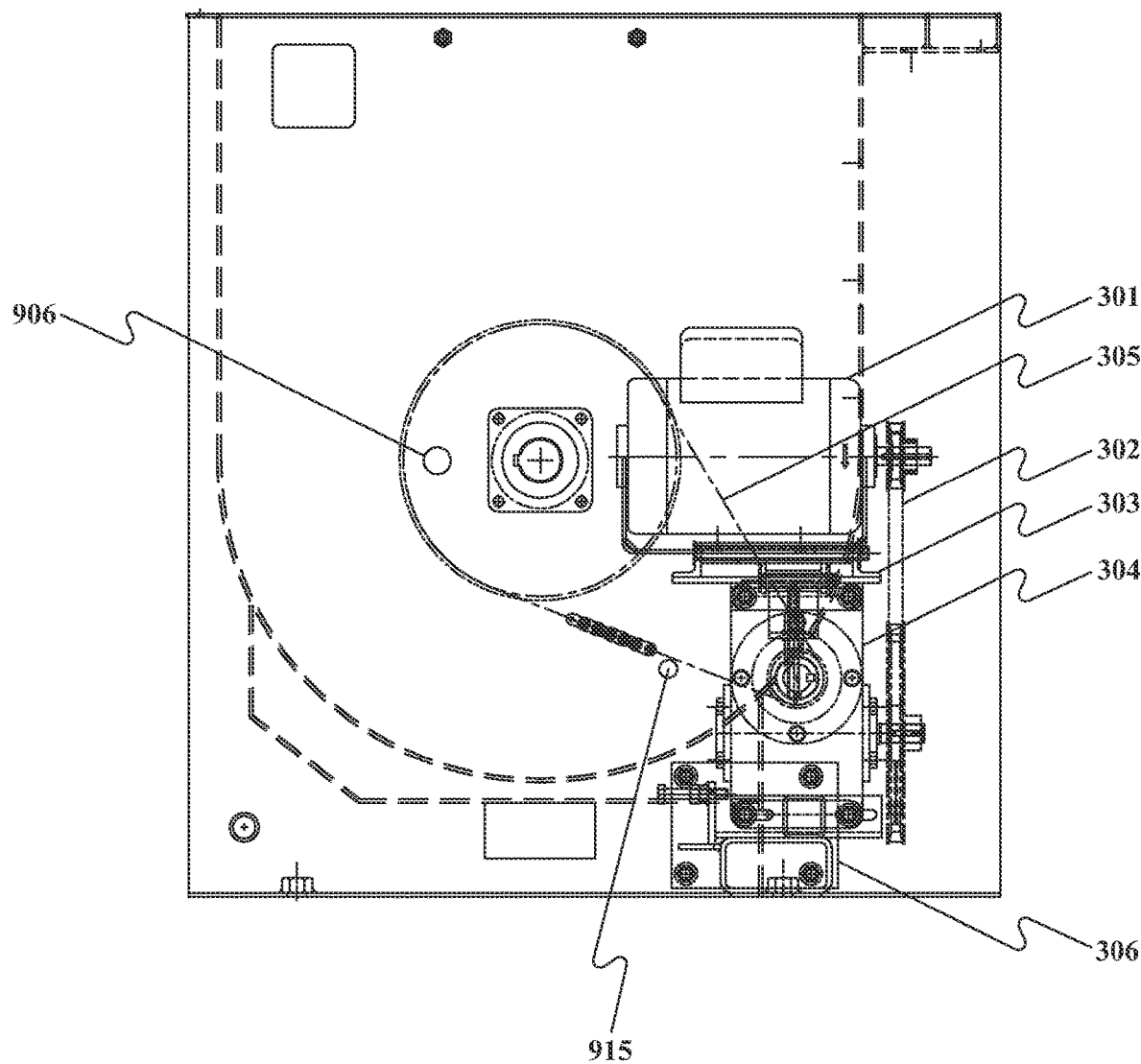
FIG. 19 is a left side view of the inner chamber similar to that previously shown in FIG. 10 and illustrating the features of the electric motor drive assembly.
Figure 20:
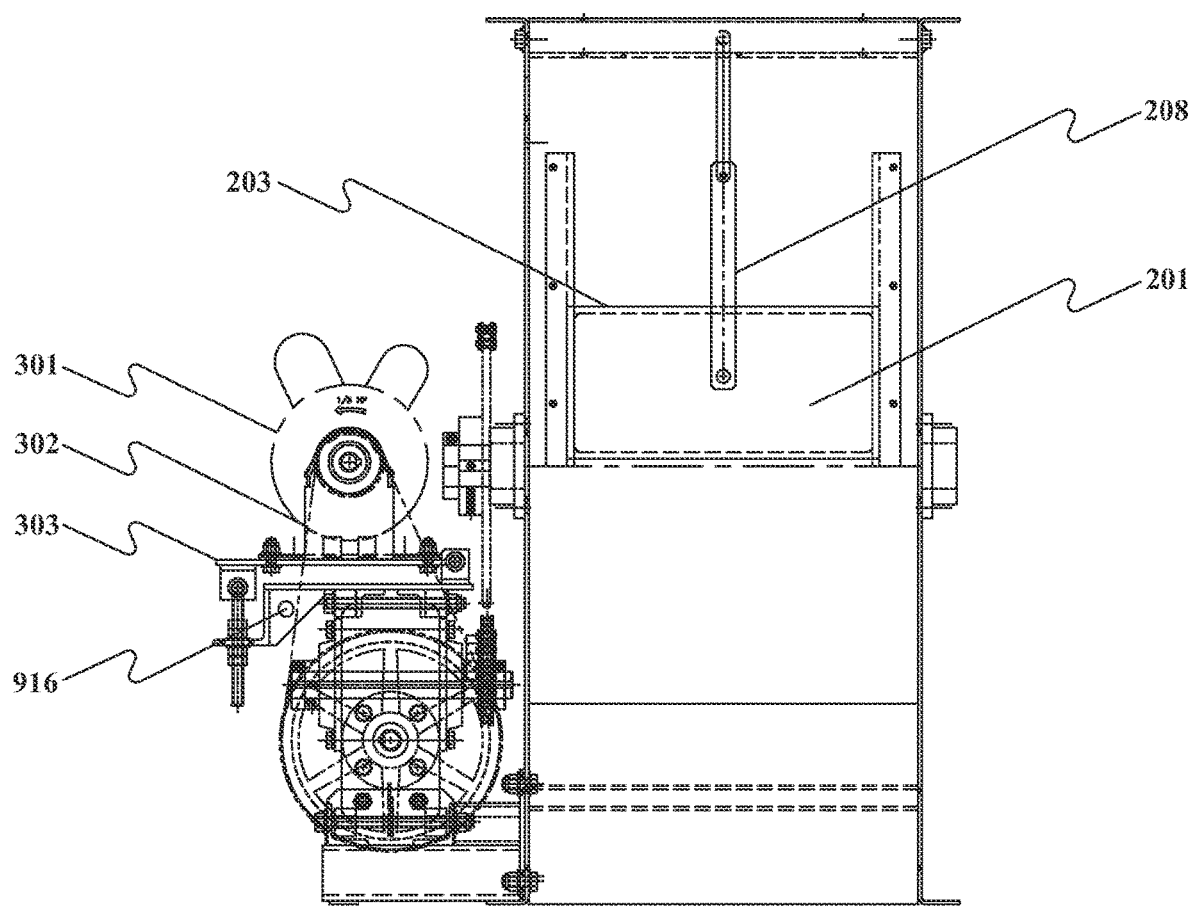
FIG. 20 is a front view of the inner chamber similar to FIG. 16 and depicting the drive assembly from another angle.

The Drive Assembly consists of an electric motor 301 (FIGS. 19 & 21) which is mounted to a speed reducer 304 (FIGS. 19 & 21) utilizing an adjustable mounting bracket 303 (FIGS. 19 & 21) the speed reducer 304 (FIGS. 19 & 21) is driven by the electric motor 301 (FIGS. 19 & 21) through a set of sheaves and a belt 301 (FIGS. 19 & 21) and the rotisserie (FIGS. 10 & 21) is driven by the output side of the speed reducer 304 (FIGS. 19 & 21) through a set of chain sprockets and a roller chain 305 (FIGS. 19 & 21), all of which is mounted to the inner chamber 200 (FIGS. 19 & 21) with a drive assembly mounting bracket 306 (FIGS. 19 & 21).

The Rotisserie consists of two (2) rotisserie bearings 401 (FIGS. 10-14) which are mounted to the inner chamber (FIGS. 10-14) with four (4) threaded fasteners each, eight (8) total, the rotisserie shaft 402 (FIGS. 10-14) is then slipped through both rotisserie bearings 401 until the minimum (such as ½ inch) extension is realized outside the rotisserie bearing on the opposite side of the drive assembly, then the rotisserie duplex finger 404 (FIGS. 10-14) is securely mounted to the rotisserie arm 403 (FIGS. 10-14) then the assembled rotisserie duplex finger 404 (FIGS. 10-14) and the rotisserie arm 403 (FIGS. 10-14) are installed through the cross hole in the rotisserie shaft 402 (FIGS. 10-14) and securely fastened the opposite end of the rotisserie arm 404 (FIGS. 10-14).

The conduction and radiant heat source 501 (FIG. 10) is installed into the opening provided on the lower left side of the inner chamber 200 (FIG. 10), which is self-locating and latching. The convection heat source 502 (FIGS. 15 & 16) is mounted inside the incoming air supply manifold 601 (FIGS. 15 & 16).

Once the convection heat source 502 (FIGS. 15 & 16) is mounted inside the incoming air supply manifold 601 (FIGS. 15 & 16), the 601 manifold is slid into the square manifold opening in the upper left side of the inner chamber 200 (FIGS. 10, 15 & 16) until it contacts the inside of the right side chamber wall at which time the air supply manifold 601 (FIGS. 15 & 16) will be secured to the right wall of the inner chamber with a threaded fastener and locking jam nut.

Next the incoming air supply blower 604 (FIGS. 15 & 16) will be mounted to the lower center of the inner chamber (FIGS. 15 & 16) and the necessary piping components will be fabricated to allow the air flow from the output end of the air supply blower 604 (FIGS. 15 & 16) to flow freely into the air supply manifold 601 air supply blower 604 (FIGS. 15 & 16), then the necessary piping components of a smaller diameter will be fabricated to allow infusing air to flow freely from the 601 air supply manifold 601 (FIGS. 15 & 16) directly into either end of the rotisserie shaft 402 (FIGS. 15 & 16), allowing the heated scavenged air to pass through the rotisserie arm 403 (FIGS. 15 & 16) directly out of the duplex rotisserie finger and into the organic waste ingredients being processed within the inner chamber.

Figure 17:
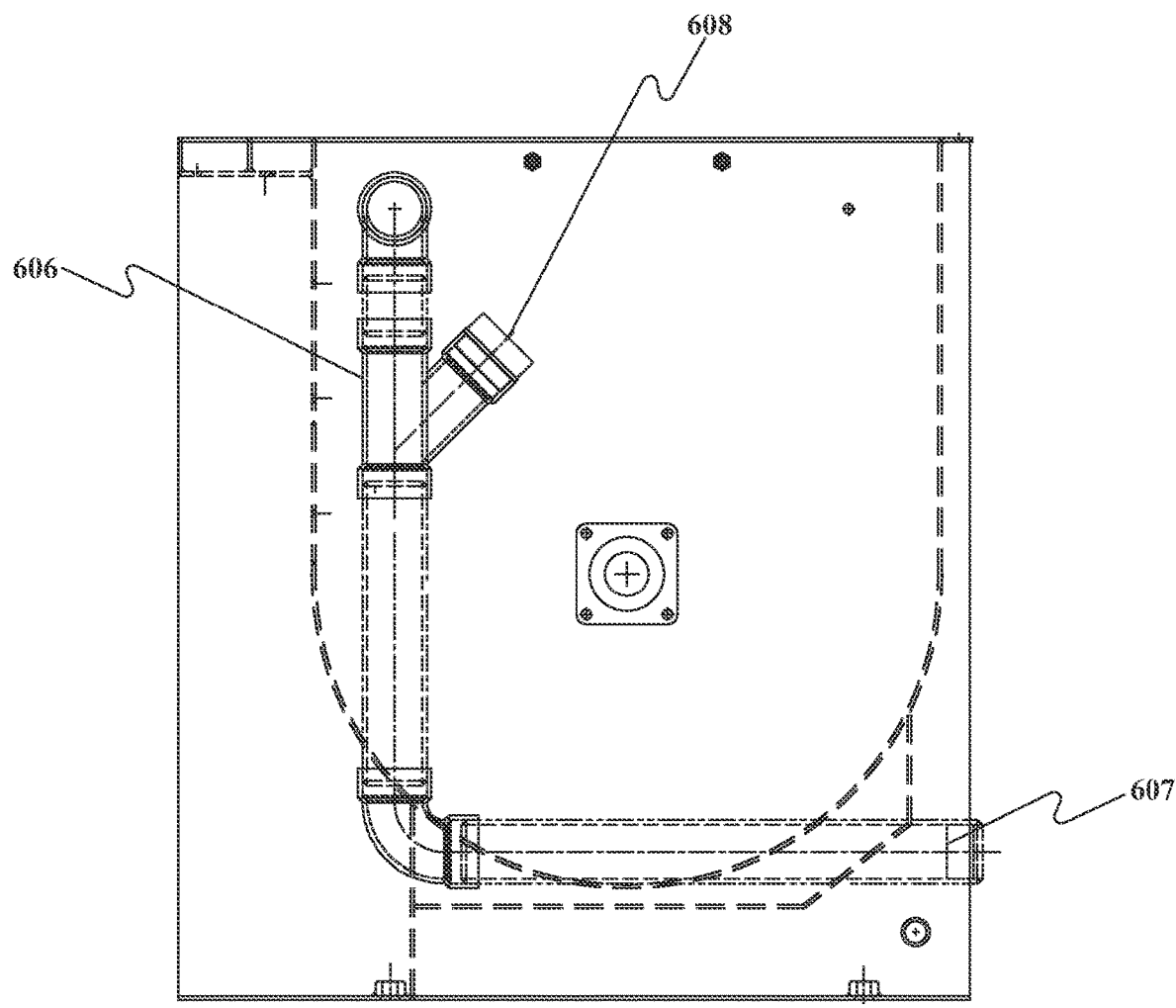
FIG. 17 is a corresponding right side view of the air entry/supply system and depicting an H2O gas vapor exhaust snorkel.
Figure 18:
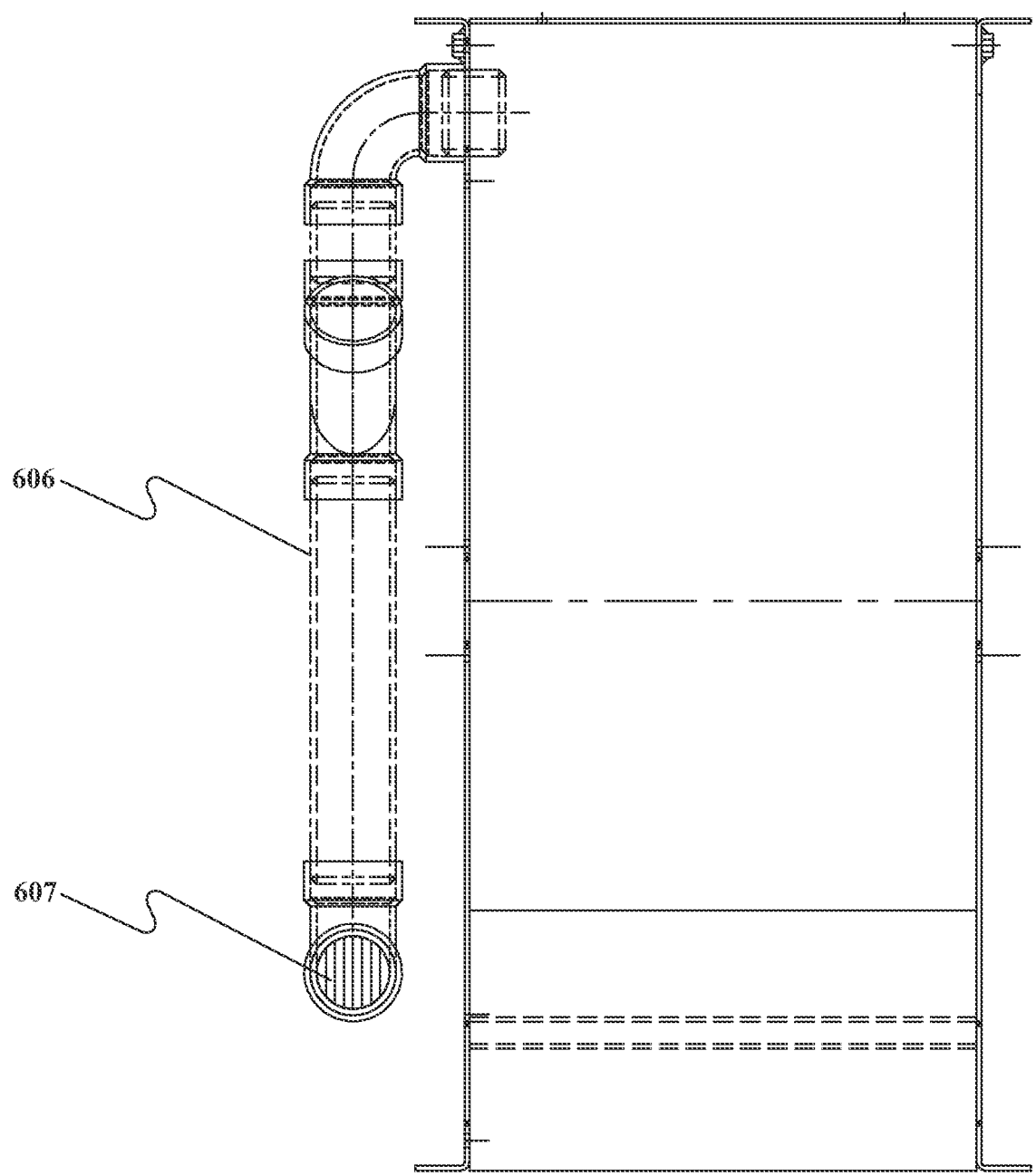
FIG. 18 is a rear view of the inner chamber and depicting the exhaust snorkel with bottom end positioned trap screen for exhausting the vapor water byproducts associated with the stabilization process.

Once the necessary piping components 606 (FIG. 17) are fabricated the upper left end is inserted and locked into the H2O gas vapor exhaust port on the right side of the inner chamber 200 wall (FIG. 13) and mounted parallel to the front and perpendicular to the bottom surface of the inner housing 200 (FIG. 17), once mounted a screen cap 607 can be inserted into the lower right end of the H2O gas vapor exhaust snorkel 606 (FIGS. 17 & 18) then the low CFM scavenging fan 608 can be installed into the upper end of the 606 "Y" component (FIG. 17).

A general description of the functionality of the controls includes either the electric relay control logic 901 or the electric CNC PC control logic 902 mounted to a location of the inner chamber with four (4) threaded fasteners (FIG. 14) as well as the control panel service plugs and wiring harnesses 918 (FIG. 14), then the rotisserie home position switch 906 is mounted to the side of the inner chamber (see FIG. 19) along with the operational drive chain switch 915 (FIG. 19). Next, the operational motor belt switch 916 is mounted to the drive assembly 300 motor reducer bracket 303 (FIG. 20), then the top load hatch integrated inner chamber illuminator 904 is mounted to the inside of the inner chamber 200 (FIGS. 14 & 21). Following this, the top load hatch integrated key lock latch and switch 903 is mounted to the front control platform of the inner chamber 200 (FIGS. 14 & 21), then the 905 unload hatch with an integrated switch (FIGS. 14 & 21) is mounted to the front control platform of the inner chamber 200 along with the humidity sensor 910 and the temperature sensor 911 (FIGS. 14 & 21).

Incorporated into such as the front top of the inner chamber are each of the cycle start switch 907, the process or unload switch 908, the relay or CNC PC selector switch 909, the emergency stop button 919, the cycle start illuminator 912, the cycle interrupter illuminator 913 and the cycle end illuminator are mounted (FIGS. 14 & 21). Once all components are mounted to the inner chamber and completely wired, the inner chamber can be installed into the outer housing 100 and secured with eight (8) threaded fasteners, four (4) each from the top and from the bottom.

In operation, and upon cycle startup the machine will display a white "start cycle "illuminator 912 out of the 104 outer housing unload port with either the 901 or 902 controller. The operator will open the outer housing load hatch 106 (FIG. 3) and load organic biomass waste ingredients and/or farm animal excrement ingredients into the inner chamber (FIG. 3), the entered organic waste ingredients immediately come to rest at the bottom of the inner chamber directly heat compartment 204 where it rests for a cycle dependent time and is heated, such as without limitation in excess of 180° F. (82.22° C.). Once the entered biomass ingredients approach thermal equilibrium with the inner chamber floor the rotisserie arm 403 and rotisserie duplex finger 404 revolve within the inner chamber for the purpose of rotating the heated organic biomass waste ingredients to its unheated side. Additionally, the rotisserie duplex finger 404 and arm 403 directly infuses heated air into the organic waste ingredients throughout the rotational cycle of the rotisserie assembly. The combined organic biomass waste ingredients will be introduced to the bottom of the inner chamber directly over the inner chamber heat compartment 204 and rest for a repetitive cycle dependent duration. Throughout the process a portion of the heated ingredients are presented to the convection heat source 502 until the cycle activates its next cycle.

This process will repeat itself for a predetermined number of cycles until such time that the humidity sensor 910 reaches its prescribed lower humidity level allowing the heat sources to stop producing heat, thus resulting in ambient air only to enter the inner chamber, thus the process then begins introducing cooling the processed organic waste ingredients until the internal end-product ingredients are measured by the temperature sensor 911 and are within a maximum of 10° F. (5.6° C.) above the ambient temperature not exceeding 80° F. (26.7° C.) at which time the temperature sensor 911 would end the flow of electricity thus deactivating all machine functions. As previously described, the ending result of the processed ingredients can be reduced to 10-15% or less of the original ingredients entered, both by weight and volume.

Once the cycle ends the machine displays a green "end of cycle" illuminator 914 that illuminates out of the 104 outer housing unload port at which time the machine is ready to unload. Unload is accomplished by the operator unlocking the top load hatch 106 & 109 (FIGS. 2 & 3) and lifting it to a full open position at which time the ingredients can be visually inspected prior to unloading specifically a process to guarantee a quality, uncontaminated end product suitable for upcycling to the source or sources it was intended. Once the operator guarantees the quality of the ingredients the operator then shifts the double locking chamber unload latch assembly 208 to the unload position and moves the cycle director switch 908 from "process" to "unload" and engages the cycle start switch selector 907 and secures the top load hatch 106 in the fully closed position at which point the machine will unload itself automatically within 3-minutes regardless of the 901 or 902 system controllers.

Should a mechanical fault be realized by the biomass stabilization machine with the control logic 901 prior to starting the machine cycle or during the machine cycle a red "cycle interrupter" illuminator will illuminate within the outer housing unload port 104, thus indicating a fault with one of the drive monitoring switches 915 and/or 916, thus requiring operator or service personnel intervention and, in the case of the CNC PC controller 902, the control panel will issue a notification, such as wirelessly to a remote processor device (e.g. handheld interface not limited to a mobile phone, tablet or the like).

The Purpose of the Invention Machine and System thereof includes the present invention provides a stabilization machine and system thereof for the purpose of converting organic biomass ingredients into a stabilized end product with an endless shelf life prospective suitable for upcycling without it ever entering the stage of decomposition. The invention and system thereof prevents organic biomass ingredients from residing as a decomposing toxic soil, water and air pollutant and food source for vermin, bacteria and diseases. Most importantly the invention machine and system thereof provides an alternative path to keeping organic biomass waste ingredients out of MSWLF (Municipal Solid Waste Landfill Facilities).

The prototype machine and system thereof as outlined in this document consistently converted fifteen (15) US gallons of organic biomass waste, particularly vegetable and fruit ingredients into a stabilized up-cyclable end product, with an endless shelf life prospective, within twenty-four (24) hours. Some ingredients processed within six (6) hours. The invention machine and system thereof processed a mixture of an assorted organic biomass vegetable and fruit waste ingredients within 16-18 hours at a minimal electrical operating cost.

The machine invention was sized based on the fact that average restaurants in my area preparing full-service sit-down food meals generated an average of fifteen (15) US gallons of waste per week or seven (7) days.

Industries suitable to accepting stabilized organic upcycled end products include for each of the following:

As referenced in FIG. 1, for stabilized Vegetable base biomass ingredients, these have been found to be suitable for the following non-limiting list of industries: natural gas refineries, crude oil refineries, biodiesel refineries, wood pellet an briquettes, fertilizer, direct soil amendment, hog and fish food pellets, stabilized hog food, campfire starter pucks, fireplace logs, coal fired electricity generation, Torre faction electricity generation and char, pyrolysis electricity generation and char production, 14. natural gas fired electricity generation, anaerobic digestion gas reclamation, direct soil amendment, cosmetics and perfumes, detergents and cleaning products, plastics and other materials, and worm bin additives.

For each of stabilized organic upcycled end products for protein base biomass (FIG. 1A), a partially recurring list of applicable industries can include each of natural gas refineries, crude oil refineries, biodiesel refineries, bone black, bone meal fertilizer, hog and fish pellets, coal fired electricity generation, Torre faction electricity generation and char production, pyrolysis electricity generation and char production, naturel gas fired electricity generation, anaerobic digestion gas reclamation, hot and fish food pellets and stabilized hog food.

For each of stabilized farm animal excrement biomass ingredients (FIG. 1C), a further partially recurring list of applicable industries can include each of natural gas refineries, crude oil refineries, biodiesel refineries, fertilizer, Torre faction electricity generation and char production, pyrolysis electricity generation and char production, anaerobic digestion gas reclamation and direct soil amendment.

By non-limiting example, one potential construction, including operational parameters, of a stabilizing machine according to the present invention can adhere to the following specifications.

BASIC SPECIFICATIONS of BMS15 Machine ONE . . . Average Commercial
- Dimensions:
  - Footprint: . . . 6.25 US square feet . . . 30 US inches square
  - Height: . . . approximately 34 US inches
  - Weight: . . . approximately 350 US pounds
- Processing:
  - Maximum processing capacity: 16 US gallons or 150 US pounds
  - Basic processing capacity: 15 US Gallons or 125 US pounds
  - Minimum processing capacity: 1 US pint or 1 US pound . . . not practical
  - Processing cycle time is ingredient dependent . . . finer food waste ingredients processes faster than coarse ingredients, as in lettuce vs asparagus . . . All food waste ingredients complete processing between 6-18 hours and horse manure processes in an average of 16-hours (all ingredients process within twenty-four (24) hours . . . the higher the water content and ingredient density the longer the process)
  - End product volumetric and weight reductions are also ingredient dependent, averaging between 80-90% weight and volume reduction
- Installation:
  - All BMS machines are designed to install outdoors . . . however, can be installed indoors
  - Required electrical service is 110/120 volts AC, 60 Hz, 15 amp outdoor GFI (Ground Fault Interrupter):
    - If the machine is to be installed INSIDE it will come with a flexible steel cord with a typical 3 prong grounded plug
- Basic Specifications of BMS15 Machine ONE and Instillation (continued)
  - If the machine is to be installed OUTSIDE an overhead water shedding roof like structure, it too will come with a flexible steel cord with a typical 3 prong grounded plug
  - If the machine is to be installed OUTSIDE without overhead water shedding roof like structure, it will need to be "hardwired" to an OUTDOOR rated GFI receptacle without a typical 3 prong grounded plug encapsulated within rubberized outdoor rated conduit
- Electromechanical Devices:
  - Electric Drive Motor: ⅓ HP single phase, 110/120 volts AC, 50-60 Hz, 326 watts & 3.4 amps running 6.8 full load amps
  - Heat system, 110/120 volts AC, 50-60 Hz, 400 watts each
  - Dry Air Intake Blower: Single phase, 110/120 volts, 60 Hz, 27.7 watts, 0.25 amps, Rated Flow Rate 60 CFM Average or 1200 CFM per cycle hour
  - Wet Air Extractor Blower: Single phase, 110/120 volts, 60 Hz, 12 watts, 0.12 amps, 12 CFM Average or 720 CFM per cycle hour
- Total Running Electric Power Usage is [0.924 kW] 924 watts maximum
- General:
  - Filtration not required
  - Liquid drainage not required
  - Hot and/or Cold water input not required
  - Leachate generation: none
  - Outgassing of ingredients being processed: NONE . . . No decomposition, NO outgassing
  - Condensate: none . . . natural evaporative steam only with a snorkel extractor
- Operating Temperatures:
  - Pathogens and bacteria are terminated upon contact within the inner chamber via the three internal conduction, radiation and convection heat sources.
  - Actual Inner chamber temperatures are:
  - inner chamber floor 200-300° F. (93.3-148.9° C.)
  - inner chamber atmosphere 100-150° F. (37.8-65.6° C.)
  - convection air 150° F. (65.6° C.)
  - Ingredient Temperatures are:
  - Product entering is ambient
  - Product processing 180-250° F. (82.2-121.1° C.)
  - Product exiting is ambient to ambient+10-15° F. (−12.22-9.44° C.)
- Staffing: operator must be able to:
- Read
- Make begin or end cycle decision and flip a switch accordingly
- Activate a cycle start switch
- Close the top load hatch and insure it's secured
- Flip unload hatch lever to process or unload position
- Work a key lock
- Differentiate between the red and green illumination signals
- Read and manage a handheld electronic device programed with machine operation variables Basic Specifications of BMS15 Machine ONE (Continued)

Machine LOAD ingredients:

Soft cell biomass particularly but not limited to vegetable and protein food waste and farm animal excrement ingredients Machine UNLOAD ingredients:

Stabilized end product biomass with an endless shelf life prospective suitable for upcycling to energy and/or fertilizer producers Additional Models:

The BMS15.9 model machine outlined within this document has been designed as a commercial restaurant machine and system thereof. Additional machines for residential and industrial applications follow the same basic features outlined herein with a variant affecting the size and power of the four aforementioned electromechanical devices whereas each machines components are identical in application and appropriately sized by a proportional formula, thus not requiring further detail outlining.

BASIC SPECIFICATIONS of BMS15.9 Machine 001 . . . Extended Commercial

Dimensions:

Footprint: . . . 9.17 US square feet

Width: . . . approximately 44 US inches

Depth: . . . approximately 30 US inches

Height: . . . approximately 34 US inches

Weight: . . . approximately 400 US pounds

Total Running Electric Power Usage is approximately [0.95 kw] 950 watts

Required electrical service is 110/120 volts AC, 50-60 Hz, 20 amp, GFI service tie-in Having described my invention, other and additional preferred embodiments will become apparent to those skilled in the art to which it pertains, and without deviating from the scope of the appended claims.

This can without limitation include slaving together a plurality of individual machines, or bodies, a first of these defining a master machine, with additional bodies further defining slaved machines such that functionality is directed from the controls of the master machine for operating any number of the slaved machines via a piggyback pigtail connection cable and virtual electronic switching and programmability. The processor controls may incorporate software protocols and algorithms which permit any of status monitoring or modification of operational parameters of any number of the individual bodies, and as determined by sensor inputs. A mobile application or other supporting platform can be provided for use on a remote processor driven device, and again is not limited to a smart phone or tablet.

The detailed description and drawings are further understood to be supportive of the disclosure, the scope of which being defined by the claims. While some of the best modes and other embodiments for carrying out the claimed teachings have been described in detail, various alternative designs and embodiments exist for practicing the disclosure defined in the appended claims.

The foregoing disclosure is further understood as not intended to limit the present disclosure to the precise forms or particular fields of use disclosed. As such, it is contemplated that various alternate embodiments and/or modifications to the present disclosure, whether explicitly described or implied herein, are possible in light of the disclosure. Having thus described embodiments of the present disclosure, a person of ordinary skill in the art will recognize that changes may be made in form and detail without departing from the scope of the present disclosure. Thus, the present disclosure is limited only by the claims.

In the foregoing specification, the disclosure has been described with reference to specific embodiments. However, as one skilled in the art will appreciate, various embodiments disclosed herein can be modified or otherwise implemented in various other ways without departing from the spirit and scope of the disclosure. Accordingly, this description is to be considered as illustrative and is for the purpose of teaching those skilled in the art the manner of making and using various embodiments of the disclosure. It is to be understood that the forms of disclosure herein shown and described are to be taken as representative embodiments. Equivalent elements, materials, processes or steps may be substituted for those representatively illustrated and described herein. Moreover, certain features of the disclosure may be utilized independently of the use of other features, all as would be apparent to one skilled in the art after having the benefit of this description of the disclosure. Expressions such as "including", "comprising", "incorporating", "consisting of", "have", "is" used to describe and claim the present disclosure are intended to be construed in a non-exclusive manner, namely allowing for items, components or elements not explicitly described also to be present. Reference to the singular is also to be construed to relate to the plural.

Further, various embodiments disclosed herein are to be taken in the illustrative and explanatory sense, and should in no way be construed as limiting of the present disclosure. All joinder references (e.g., attached, affixed, coupled, connected, and the like) are only used to aid the reader's understanding of the present disclosure, and may not create limitations, particularly as to the position, orientation, or use of the systems and/or methods disclosed herein. Therefore, joinder references, if any, are to be construed broadly. Moreover, such joinder references do not necessarily infer that two elements are directly connected to each other.

Additionally, all numerical terms, such as, but not limited to, "first", "second", "third", "primary", "secondary", "main" or any other ordinary and/or numerical terms, should also be taken only as identifiers, to assist the reader's understanding of the various elements, embodiments, variations and/or modifications of the present disclosure, and may not create any limitations, particularly as to the order, or preference, of any element, embodiment, variation and/or modification relative to, or over, another element, embodiment, variation and/or modification.

It will also be appreciated that one or more of the elements depicted in the drawings/figures can also be implemented in a more separated or integrated manner, or even removed or rendered as inoperable in certain cases, as is useful in accordance with a particular application. Additionally, any signal hatches in the drawings/figures should be considered only as exemplary, and not limiting, unless otherwise specifically specified.

The invention claimed is:

1. A biomass stabilization assembly for managing a soft cell organic material, comprising:

a body including an outer housing having a loading port for communicating a volume of the organic material to an inner chamber;

a drive sub-assembly for operating a rotisserie located within said inner chamber for agitating the organic material;

each of a heat source and an air supply communicated to the organic material within the inner chamber;

an exhaust withdrawing from the inner chamber a fluid vapor emitted from the organic material; and a controller mounted in said body including a control logic having an arrangement of temperature and humidity sensors and switches for operating each of said drive sub-assembly, heat source, and air supply over repetitive cycles until said humidity sensor reads a prescribed lower humidity level, at which point said controller deactivates said heat source, resulting in only ambient air of said air supply entering said inner chamber to cool the organic material until it reaches a temperature within 10° F. above ambient temperature not exceeding 80° F., at which point said temperature sensor instructs said controller to deactivate all functions of said assembly, with the organic material being reduced to 10-15% of its original weight and volume.

2. The assembly of claim 1, said loading port further comprising a top hatch formed in said outer housing, unloading of the stabilized material occurring through any of a side or bottom hatch or chute.

3. The assembly of claim 1, said body exhibiting any of a rectangular or cuboidal shape and being supported upon a plurality of castor wheels.

4. The assembly of claim 1, said heat source further comprising each of a conduction and radiant source communicated to said inner chamber and a convection heat source communicated to said air supply.

5. The assembly of claim 1, said drive assembly further comprising an electric motor and reducer drive assembly for operating a drive shaft of said rotisserie.

6. The assembly of claim 5, said rotisserie further comprising a rotisserie arm extending from said drive shaft, at least one duplex finger secured to an end of said rotisserie arm, a manifold extending to said inner chamber for allowing direct infusing of said air supply into the organic material.

7. The assembly of claim 6, further comprising said at least one duplex finger adjusting an angle of perpendicularity to said drive shaft.

8. The assembly of claim 6, said air supply further comprising a blower communicating with said inner chamber.

9. The assembly of claim 1, said controller further comprising electronic frequency broadcasting to advance machine cycle requirements.

10. The assembly of claim 9, further comprising said controller communicating wirelessly with a remote processor device for enabling remote operation.

11. The assembly of claim 1, further comprising a power supply for operating said drive sub-assembly and said controls, said power supply including either of a power service plug or a hard wiring connection.

12. The assembly of claim 11, further comprising said power supply operating under 1 kw per hour.

13. The assembly of claim 1, said controller further comprising a prewired modular control panel complete with electrical plugins and harnesses.

14. The assembly of claim 1, further comprising a duration of a biomass stabilization operation being no more than twenty four hours.

15. The assembly of claim 1, said body further comprising a master machine, a plurality of additional bodies further defining slaved machines directed from said controller of said master machine for operating any number of said slaved machines via a piggyback pigtail connection cable and virtual electronic switching and programmability.

16. The assembly as described in claim 15, further comprising a mobile application for use on a smart phone or tablet for operating said controller.

17. The assembly as described in claim 1, further comprising a recirculation sub-system for redirecting scavenged heated air back into said heat source.

18. The assembly as described in claim 1, further comprising said body exhibiting any of a rectangular or cuboidal shape and being supported upon a non-heat transferring bunks adapted for use on earth, gravel and/or asphalt.

* * * * *